(12) United States Patent
Castillo et al.

(10) Patent No.: US 8,845,181 B2
(45) Date of Patent: Sep. 30, 2014

(54) MIXING SYSTEM INCLUDING A FLEXIBLE BAG, SPECIFIC FLEXIBLE BAG AND LOCATING SYSTEM FOR THE MIXING SYSTEM

(75) Inventors: Jose Castillo, Brussels (BE); Florence Bosco, Mignault (BE); Samuel Osumba, Brussels (BE)

(73) Assignee: Pall Artelis BVBA, Brussels (BE)

( * ) Notice: Subject to any disclaimer, the term of this patent is extended or adjusted under 35 U.S.C. 154(b) by 0 days.

(21) Appl. No.: 13/615,727

(22) Filed: Sep. 14, 2012

(65) Prior Publication Data

US 2013/0121103 A1 May 16, 2013

Related U.S. Application Data

(63) Continuation of application No. 12/444,040, filed as application No. PCT/EP2007/053998 on Apr. 24, 2007, now Pat. No. 8,282,267.

(30) Foreign Application Priority Data

Oct. 3, 2006 (WO) .................. PCT/EP2006/066980
Apr. 12, 2007 (WO) .................. PCT/EP2007/053595

(51) Int. Cl.
*B01F 15/00* (2006.01)
*C12M 1/00* (2006.01)
*B01F 13/08* (2006.01)
*B01F 7/16* (2006.01)
*C12M 1/06* (2006.01)
*B01F 3/12* (2006.01)

(52) U.S. Cl.
CPC ............ *B01F 15/0085* (2013.01); *C12M 23/14* (2013.01); *C12M 27/20* (2013.01); *B01F 13/0827* (2013.01); *B01F 13/0818* (2013.01); *B01F 7/1635* (2013.01); *C12M 27/02* (2013.01); *B01F 3/1221* (2013.01); *C12M 23/50* (2013.01); *B01F 15/00831* (2013.01)
USPC ........... 366/247; 366/134; 366/195; 366/168; 366/307

(58) Field of Classification Search
USPC ............... 366/134, 247, 195, 168.1, 306–307
See application file for complete search history.

(56) References Cited

U.S. PATENT DOCUMENTS

| | | | | |
|---|---|---|---|---|
| 3,647,397 A * | 3/1972 | Coleman | .................... | 366/167.1 |
| 4,488,817 A * | 12/1984 | Uesaka et al. | ................ | 366/149 |
| 4,622,085 A * | 11/1986 | Yamada et al. | ................. | 156/94 |
| 5,727,878 A * | 3/1998 | Sullivan, Jr. | ................... | 366/247 |
| 5,803,137 A * | 9/1998 | Shimotoyodome et al. | ..... | 141/67 |
| 7,481,572 B2 * | 1/2009 | Terentiev | ...................... | 366/279 |
| 7,762,716 B2 * | 7/2010 | Terentiev et al. | ............. | 366/273 |
| 8,123,199 B2 * | 2/2012 | Terentiev et al. | ............... | 261/93 |
| 8,282,267 B2 * | 10/2012 | Castillo et al. | ................ | 366/262 |

(Continued)

OTHER PUBLICATIONS

U.S. Appl. No. 13/615,746 Office Action dated Jul. 16, 2013.

(Continued)

*Primary Examiner* — Joseph S Del Sole
*Assistant Examiner* — Nahida Sultana
(74) *Attorney, Agent, or Firm* — King & Schickli, PLLC

(57) ABSTRACT

Mixing system comprising: a flexible bag (28) with a mixing device (1) comprising a magnetic impeller; and an alignment facilitation device adapted to facilitate alignment between the magnetic impeller and a magnetic driver (36) located external to the system. Specific flexible bag and hardware therefore.

22 Claims, 24 Drawing Sheets

(56) References Cited

U.S. PATENT DOCUMENTS

| | | | |
|---|---|---|---|
| 8,282,269 B2 * | 10/2012 | Terentiev | 366/279 |
| 8,292,491 B2 * | 10/2012 | Castillo et al. | 366/273 |
| 8,500,322 B2 * | 8/2013 | Morrissey et al. | 366/273 |
| 8,556,497 B2 * | 10/2013 | Morrissey et al. | 366/273 |
| 2004/0062140 A1 * | 4/2004 | Cadogan et al. | 366/144 |
| 2004/0190372 A1 | 9/2004 | Goodwin et al. | |
| 2005/0002274 A1 | 1/2005 | Terentiev | |
| 2007/0253287 A1 | 11/2007 | Myhrberg et al. | |
| 2010/0128555 A1 * | 5/2010 | Hughes | 366/132 |

OTHER PUBLICATIONS

U.S. Appl. No. 13/615,746 Office Action dated Mar. 12, 2013.

* cited by examiner

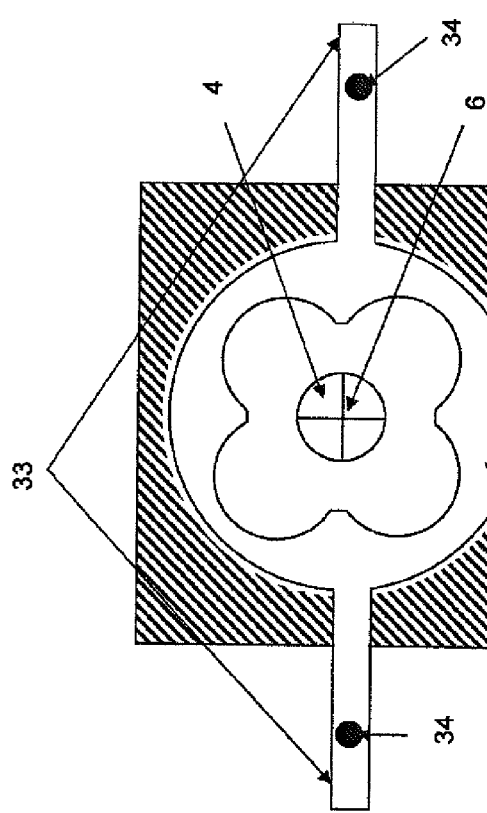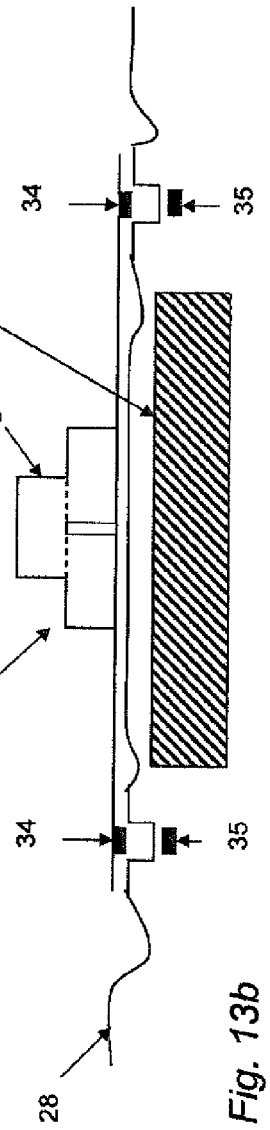
Fig. 13 a
Fig. 13b

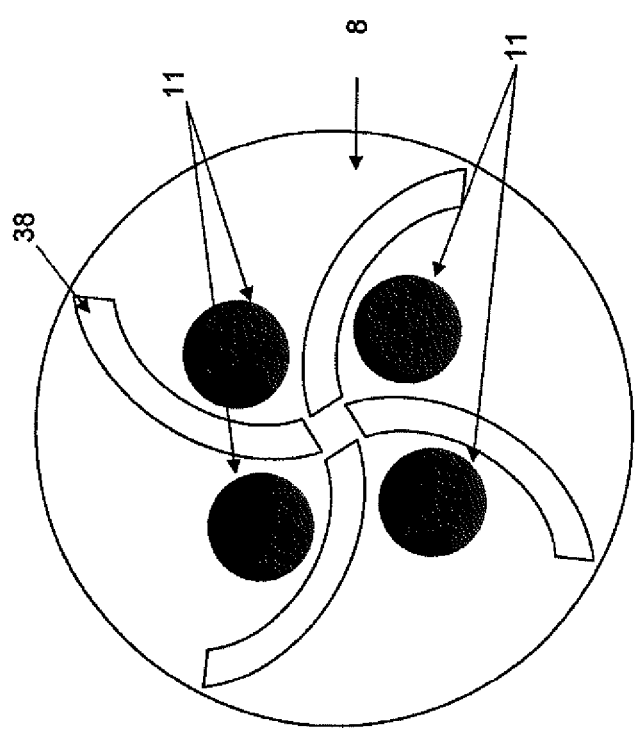
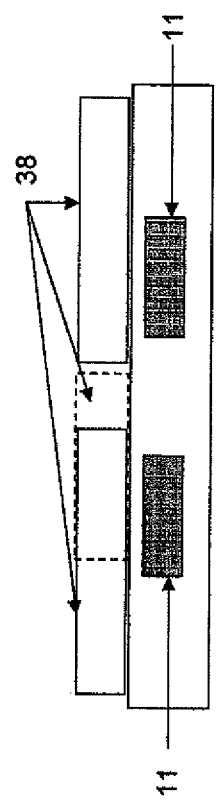
Fig. 15 a
Fig. 15 b

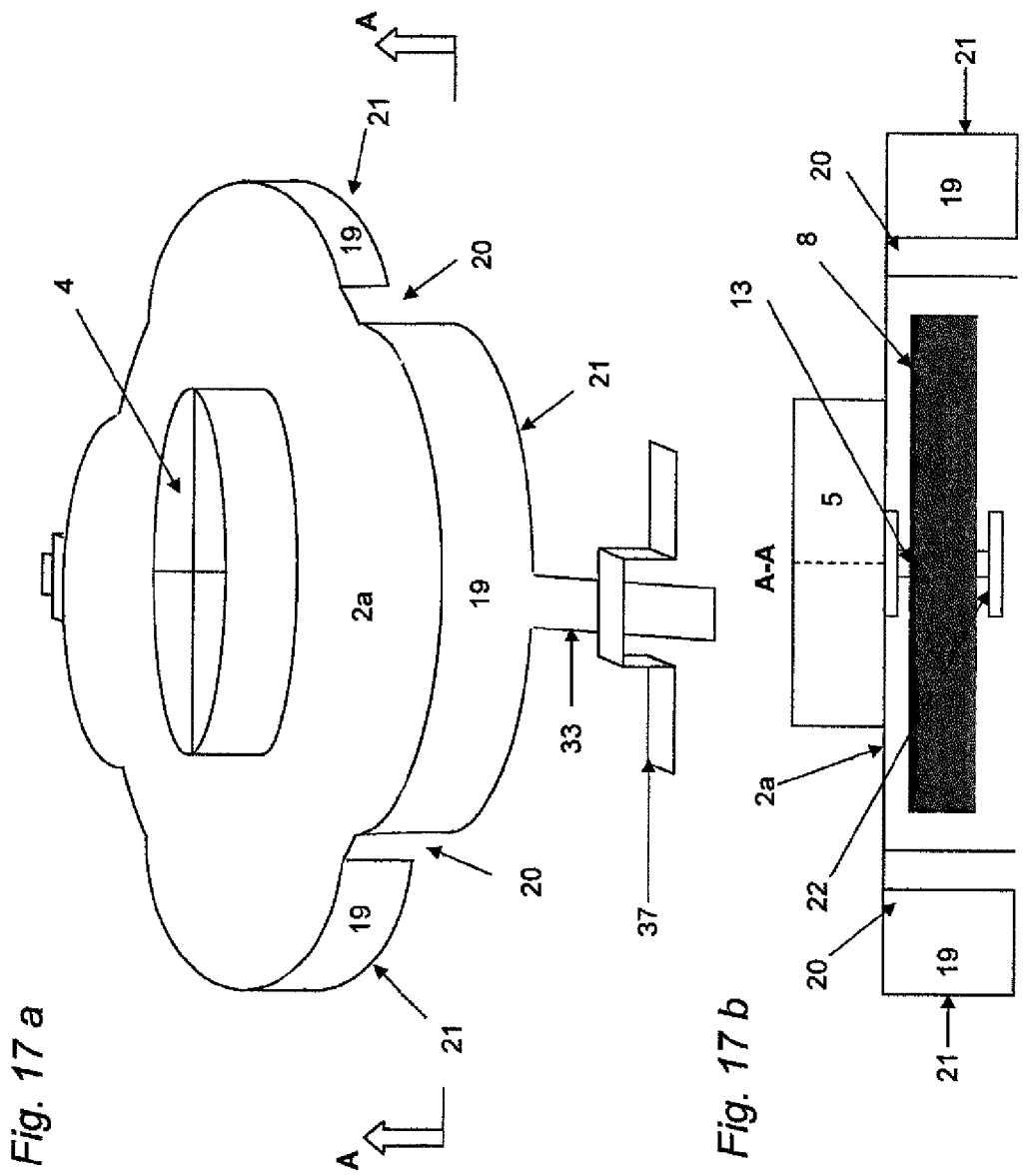

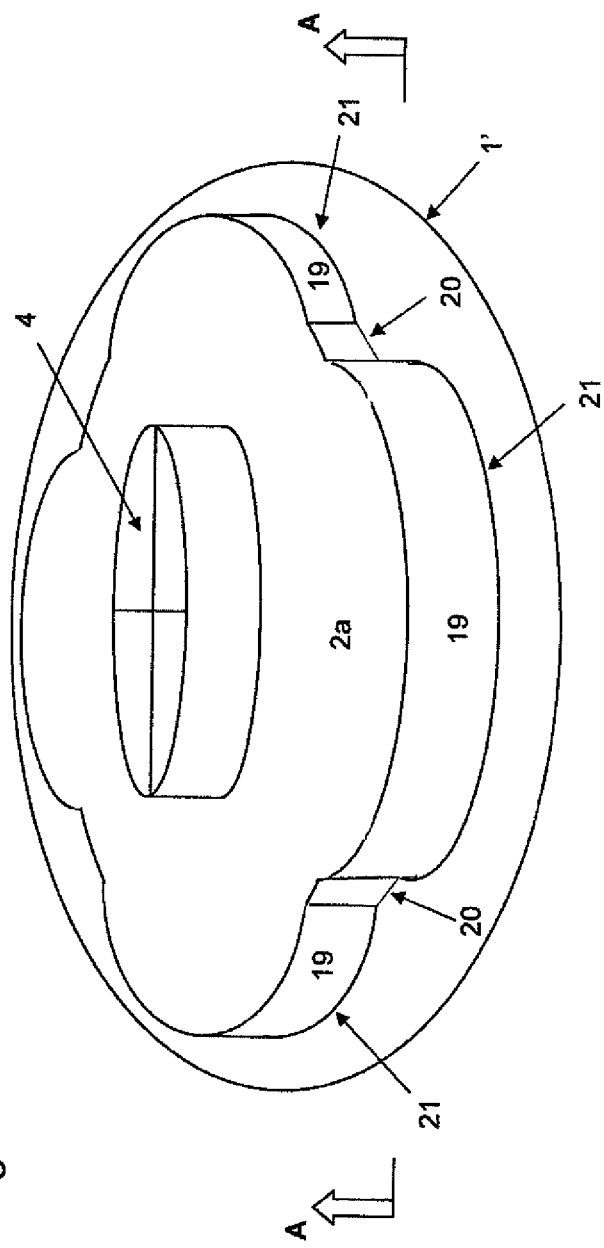
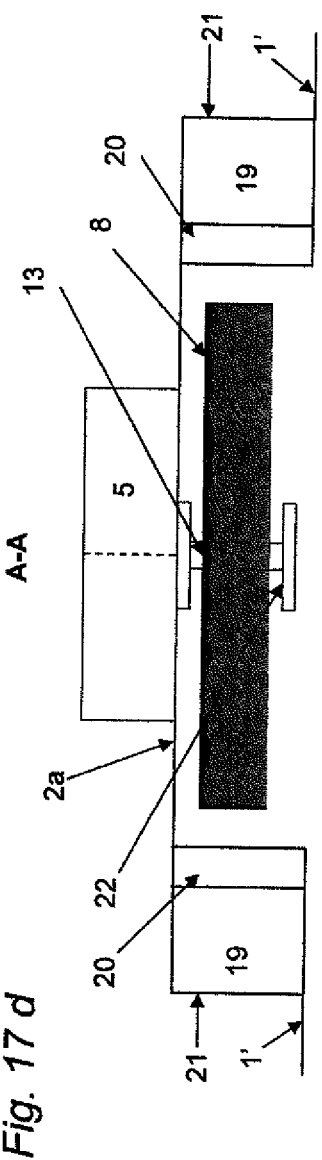
Fig. 17c
Fig. 17d

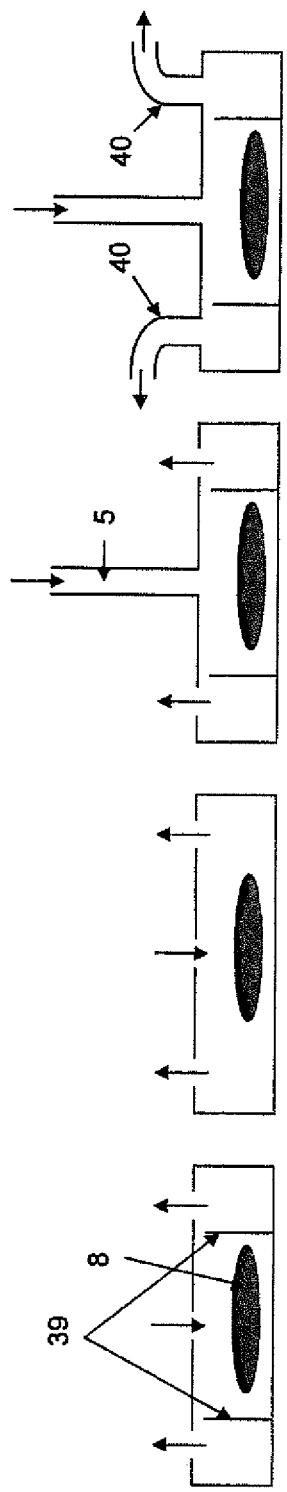

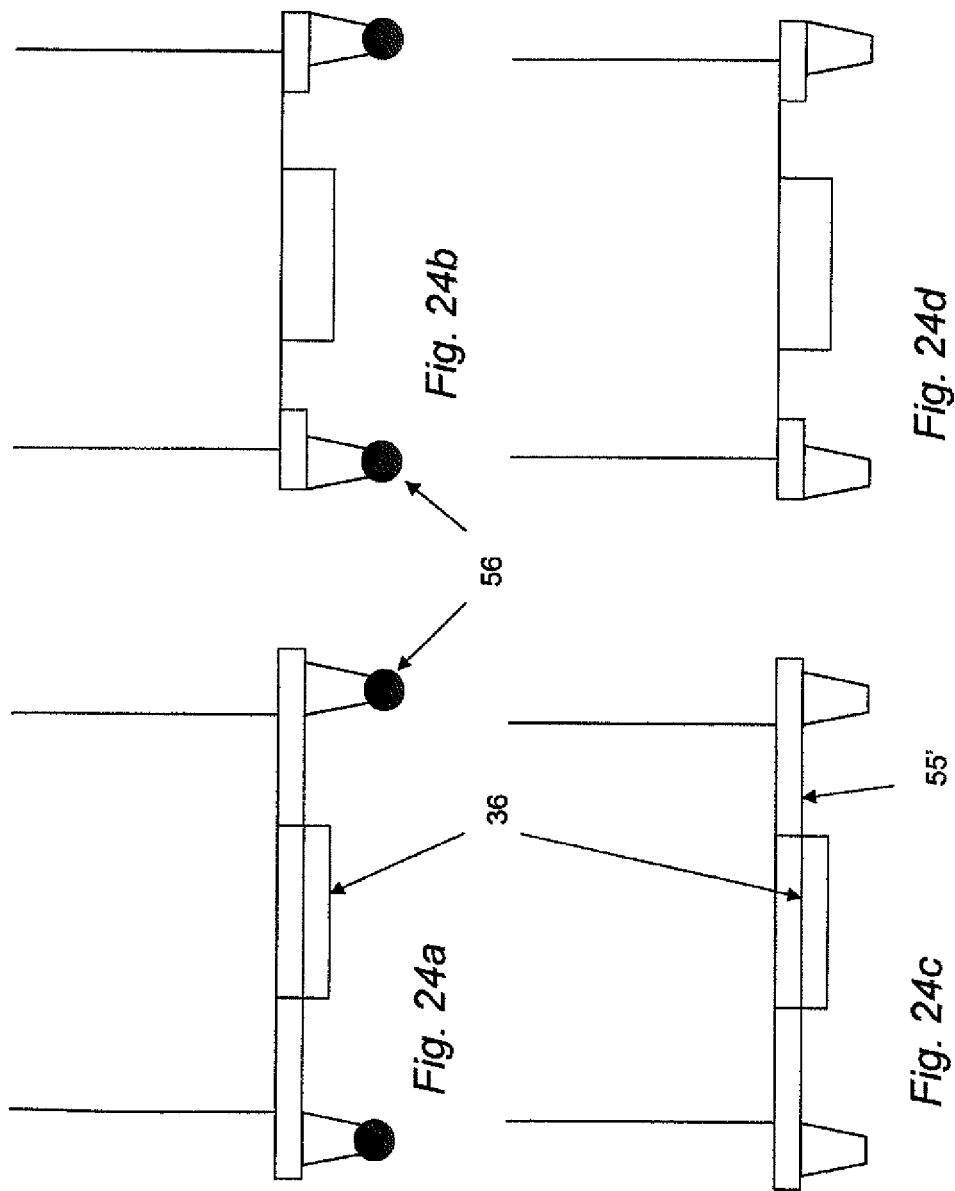

MIXING SYSTEM INCLUDING A FLEXIBLE BAG, SPECIFIC FLEXIBLE BAG AND LOCATING SYSTEM FOR THE MIXING SYSTEM

This application is a continuation of U.S. patent application Ser. No. 12/444,040, filed on Apr. 2, 2009, the disclosure of which is incorporated herein by reference.

In a first aspect, the present invention relates to a mixing system including a flexible bag; to a specific flexible bag intended therefore and to specific hardware related thereto.

The mixing and/or suspension of solutions is required in many technical fields such as biotechnology, pharmaceuticals and medical.

For example, in the field of the biotechnology and pharmaceutical industry, it is often necessary to prepare and to complement solutions, buffers, culture medium, suspensions, etc (referred to in general terms hereinafter as liquid substances).

More specifically, some specific applications of circulation/mixing devices include dilution, dissolution and/or adjusting pH, salinity conditions, concentration, osmolality, temperature, of a liquid substance of any kind (buffer, culture medium, saline solution, etc.).

To be safe and effective for their intended use, solutions of culture media, buffers, reagents, etc. used in these fields must be pure and sterile. Accordingly, the mixing tank, mixing device, and all other reusable components that contact the solution must be carefully cleaned after use to avoid any cross contamination with subsequent batches of solutions. The cleaning of the structural components is labour-intensive, time-consuming, and costly.

In order to avoid these cleaning steps, single use "mixing bags" have been developed. These are disposable flexible bags provided with a mixing device and intended to be supported in a rigid container.

Mixing bags are already widespread in the bio-production market mostly for storage applications. The rigid containers used to handle them are designed to be stacked and fork lifted which are two requirements for automated stock management. In most of the case, the user is already equipped with large number of standard containers. So there is a need to supply the user with a flexible bag mixing solution to allow preparation directly in the storage bag.

In these mixing bags, the mixing device preferably is a magnetic stirring device which is driven by an external driver positioned outside of the bag and that may be part of or fixed to the rigid container. By doing so, there is no risk of contamination of the contents of the bag from the outside. Even more advantageously, said device comprises a magnetic impeller rotating around a fix rotational axis and not a mere stir bar so that it can rotate at higher speed with less risk of decoupling from its driver.

The motive device or driver and the impeller of the magnetic stirring device both include permanent magnets designed to have the best coupling so the higher torque transmission. Beside the design of the permanent magnets, the alignment is crucial for the coupling. The design of the permanent magnets can be as good as possible, if the magnets of the motive device are not aligned with those of the impeller, torque can not be transmitted between both.

This requirement and other needs for improved mixing systems can be summarized as follows:

Achieve alignment without specific holes or any type of relieves in the rigid container to make the use of containers as standard as possible. Allow the use of a commercial standard magnetic driver without customization.

Achieve compatibility with automated stock management, stacking and forklift.

Allow spray sanitization of the system. Materials, as well as design are selected to face hard chemical conditions during sanitization of clean rooms (by using formaldehyde or hydrogen peroxide).

Achieve integration of the motive device and control unit in an integrated system.

Allow the driver to be removable from its functional location once the mixing job is finished for short or even long term storage. There is no point in storing the motive device with the container and it would require a large number of motive devices.

Prevent tubing from touching the floor underneath the tank: tubing security.

Patent application US 2005/0002274 discloses a way to align a magnetic impeller located in a bag supported in a rigid container with its driver, said way consisting in providing a locator projection to a rigid portion which is part of the bag (sealed on an opening in said bag) and providing the driver with a matching cavity for receiving said projection. This way of coupling doesn't allow standard equipment (container and driver) to be used since the container must comprise an opening for the projection and since the driver must comprise a cavity or a corresponding relief to match the one of the projection.

Patent application WO 2006/002091 also describes a system which allows alignment between a magnetic impeller located in a bag supported in a rigid container and its driver. This system includes a connecting piece (interface) between a locator projection extending from the bag close to the impeller and a part of the driver through an opening in the rigid container. It also includes a wheeled cart guided by rails in order to position the driver relative to the interface. The drawbacks of that system are the following:

The rigid container has to be opened on its bottom for coupling through it. This container can't be used for other applications, as for example the use of standard storage bags. The motive device might also need a customization.

These containers can not be stacked on another and in addition their form is not well adapted to be transported by an elevator. There are also very bulky.

No tubing security

Two fixation operations are required: fixing the intermediate piece to the bag and then, fixing the driver to said piece.

The present invention aims at solving these problems by providing a system where the driver is removable easily so that the bag and its container are storable apart; where the rigid container is standard and hence, compatible with automated stock management, and doesn't require an opening to be made for mechanical coupling between the mixing device and its driver, or at least one part of the bag, the container and/or the driver; and finally, it is a solution which is simple, requires only one fixation operation and allows easy integration of tubing security.

It is based on the finding that working without mechanical engagement (either direct or indirect using intermediate connecting piece) is possible and even with high precision of alignment of the driver towards the magnetic impeller. It can namely be achieved by either locating both very precisely relative to each other and/or relative to the rigid container or by allowing the mixing device to auto align itself with the driver.

Accordingly, the present invention relates to a mixing system comprising:
- a flexible bag with a mixing device comprising a magnetic impeller; and
- an alignment facilitation device adapted to facilitate alignment between the magnetic impeller and a magnetic driver located external to the system.

According to a preferred embodiment, the mixing system of the invention comprises a rigid container in which the flexible bag can be retained, said container having no specific aperture that functions to aid in the coupling between the mixing device and the driver.

Preferably, the alignment is not merely accomplished by mechanical engagement or mating between the bag and the external magnetic driver or some connecting portion disposed there between. Instead, it is preferably achieved by either locating both very precisely relative to the rigid container or by allowing the mixing device to auto align itself with the driver.

According to the invention, the terms "flexible bag" designate a bag or pouch made of walls of similar structure preferably assembled by welding. These walls may be made of a mono- or multilayer film including, or not, a barrier layer based on a bather polymer like EVOH (ethylene vinyl alcohol polymer). Generally, these films may have an inner layer (in contact with the contents of the bag when filled) based on a polyolefin, preferably an ULDPE (ultra-low density polyethylene, pref. medical grade).

The bag may be of cylindrical shape although cylindrical flexible bags are not easily baffled and difficult to manufacture. A bag with a cubic or parallel-piped shape is preferable namely because it works as a baffled tank.

The flexible bag according to the present invention is equipped with a magnetic mixing device. Although any kind of mixing device including a magnetic impeller may be used, preferably, it is a device wherein liquid flow is well organized i.e. the liquid enters through specific opening(s) and leaves through other specific opening(s), the former being located centrally and the latter, peripherally. "Specific" means that a given opening only acts as inlet or outlet opening and not as both. The terms "central" and "peripheral" are to be construed as being complementary i.e. "peripheral" means decentralized.

Preferably, the mixing device comprises a rotary magnetic impeller located in a compartment delimited by a wall, said mixing device further comprising:
- at least one liquid inlet opening located in a central area of the wall;
- at least one liquid outlet opening located in a peripheral area of the wall; and
- deflecting means that substantially alter the natural rotational direction of the liquid exiting the outlet opening.

Normally (without deflecting means), when the liquid exits the compartment of the mixing device, its flow path is tangential to the wall of the compartment at the outlet point. The deflecting means of this aspect of the invention act to shift this liquid outflow path from a given angle after the liquid has impacted on the deflecting means so that said flow path tends to become more radial (i.e. the flow direction when the liquid leaves the deflecting means tends to become more parallel to the radial direction at the outlet point).

This angle shift is preferably of at least 5°, more preferably of at least 10° and even more preferably of at least 20°. It preferably allows directing the liquid outflow in any preferred direction, for instance the corners of the parallelepiped-shaped containers in general and flexible bags in particular. These corners are well known to persons of ordinary skill in the art as being dead zones in a mixing process. By this angle shift at each of the defection means, the global flow pattern created by the mixer within its action area is changed from a circular path to several divergent jets, the number of jets being equal to the number of outlets.

This directional change of the velocity vector occurs directly when said flow leaves (is no longer in contact with) said deflecting means. This permits mixing of the substance away from the mixing device and throughout the bag in a more efficient manner. It allows avoiding dead zones for instance in the corners of the container (bag) to be mixed.

In the mixing device, there are preferably several outlet openings, the number of which depending in fact on the size and shape of the container it is designed for. These outlets are preferably located on a side portion of the wall of the mixer. They are preferably all identical. Advantageously, they are all equipped with deflecting means and even more preferably, with identical deflecting means so that the flow pattern is symmetrical. The terms "equipped with" mean in fact that there are some deflecting means somewhere in the flow leaving the outlet opening but not necessarily directly at said opening.

The wall of the mixing device may be a continuous surface without angles like a bell which would be fixed to or lie on a bag wall by the open end thereof. In that embodiment, the rotational axis of the magnetic impeller may be fixed to the top of the bell so that there is no bottom surface needed.

Alternatively, said wall may be a kind of box comprising different walls defining angles between each other and/or comprising a cover and side walls which may be welded and/or otherwise assembled to each other (for instance by a snap fit system). It may also comprise a bottom surface although this is not mandatory if the rotational axis of the impeller is fixed to the cover (top of the wall).

Hence, in a preferred embodiment, the mixing device comprises a wall delimiting a compartment with a top surface where the magnetic impeller is located, said wall comprising no bottom surface and having a rotational axis for the impeller fixed to its top surface.

It is worth noting that although the above embodiment (of a mixing device without bottom surface and having its impeller fixed at the top surface) has been described in the frame of the present invention, it is advantageous in any magnetic mixing system driven from outside for the reason mentioned below (maximum torque transmission because the driver can be put closer to the impeller).

In another preferred embodiment, which may be combined with the former one, the mixing device includes sidewall portions with or forming one or more outlets, the side wall portions preferably including deflector portions positioned and shaped to deflect liquid substance as it exits the outlets.

The wall (portions) of the mixing device are preferably made of plastic and even more preferably, made of a plastic compatible with the contents of the bag and their use (e.g., a medical grade of a chemically resistant polymer like HDPE). Preferably, this plastic is rigid in order to allow pressure build up without deformation. If the mixing device is to be welded to the bag, the parts of the wall(s) that must be welded on it are preferably of a material compatible with it. Considering the layout of the industrial films set forth above, a polymer of ethylene is a good choice. Preferably, a HDPE (high density polyethylene) is used because other polymers like EVA (Ethylene Vinyl Acetate copolymer) or LDPE are not rigid enough.

The magnetic impeller in the mixing device according to the invention is a part comprising magnet(s) and which rotates in a compartment around a central axis which is either fixed on/part of the bottom of the compartment (in the case it has one) or of the top thereof. This axis may comprise two separate pins extending from a ring (as disclosed in U.S. Pat. No. 4,162,855, the content of which is incorporated by reference in the present application). Alternatively, it may be a single axis passing through a hole in the rotary magnetic element.

This impeller may merely be a stir bar (so an impeller with two straight arms only) or it may comprise at least three arms which may be straight or curved (although this may not allow rotation in both directions) or may comprise curved portions. They may also have sections in the shape of parallelograms. It may also be in the shape of a cross (or plus sign) or of a disc in which magnet(s) are embedded symmetrically versus the rotation axis. This disc preferably wears an upper relief in the form of paddles which are preferably straight (not curved) so that the disc can rotate in both directions with identical performances. In fact, the invention applies to all kinds of impeller geometries.

Whatever its shape, the decoupling of the impeller from its rotational axis (at high rotation speed or during shipping and handling) can be avoided by providing adequate securing means on the axis. The securing means may be an adequate relief of the end of the axis (such as a cross shaped portion for instance, the axis being inserted in the hole of the element by its other extremity). The securing means may also be a plug (blocking plate with fixation means) fixed on top of the axis after said axis has been inserted into the hole of the rotary element.

The rotational axis preferably comprises a protrusion from the bottom of the mixing device or of the bag (if the mixing device has no bottom) or from the top of the mixer, said protrusion being equipped with a bearing which fits in a corresponding hole of the rotary magnetic element. In that embodiment, the protrusion preferably comprises embossings (generally in the number of three or six, six being preferred) or has the shape of a cross to provide a tension plugging and a perfect fitting between protrusion and bearing and to block rotation of said bearing.

In order not to loose magnetic forces and hence, torque transmission, the magnetic impeller is preferably located as close as possible relative to the bottom of the bag without touching it however (to avoid friction). Hence, it is preferably positioned at less than 10 mm of the bag bottom. In that regard, the embodiments described earlier where the wall of the mixing device has no bottom surface are advantageous because it suppresses the bottom wall of the mixing device, which may lead to a gain of up to 2 mm.

In a preferred embodiment of the invention, the flexible bag comprises at least 2 facing walls and the mixing device is located inside of it on one of said walls, the other facing wall comprising a protective cover having a cavity matching the external shape of the mixing device. This cover is preferably fixed (preferably by welding) on an opening of said wall.

The term "matching" means in fact that the mixing device fits (can be inserted) inside the cover and can be removed there from i.e. that the mixing device has smaller dimensions and an adequate shape to be able to be received (preferably completely) inside the cover.

This embodiment prevents the bag from being damaged owed to the presence of a rigid mixing device inside of it. It also allows the mixing device to be kept in place during shipping and handling when said mixing device is not fixed to the bag (see above).

The mixing system of the invention generally comprises a rigid container which retains (supports) the flexible bag. This container may be of any shape provided the bag fits therein (i.e. can lie on its bottom and press on its side walls when it is filled with liquid). Preferably, it is a container with at least five plain walls (one bottom and four side walls) which may have openings. Preferably, the inner size of the container matches substantially the outer size of the flexible bag so that hydrostatic pressure can be supported by its walls. It is preferably made of a metal like stainless steel, stainless steel 316 being particularly suitable. Nevertheless it could be made of plastics as well.

Generally, the container comprises a bottom plate to which four side walls are assembled. Generally, bottom plate and side walls are sheets of about less than 5 mm thickness (said thickness being adapted to the size and hence, volume of the container). These walls may be a single sheet folded in a cubic or parallelepiped shape. They advantageously have a folded back portion at their top in order to increase the resistance in torsion of the assembly. The bottom plate may be in the shape of a frame on which an additional sheet will rest to from the bottom of the container. Hence, the container generally has a beam extending downwards at its periphery.

According to the invention, the magnetic driver used to induce rotation of the magnetic impeller of the system is located outside said system, generally below it (i.e. below the bottom of the rigid container if there is one). Any kind of commercial magnetic driver can be used provided it has enough torque transmission (preferably up to 1 Nm) and speed possibilities (preferably up to 1500 rpm). Its size and shape are preferably such that it can fit underneath the container without modifying it or said container.

This driver may be fixed to/part of the system. However, as explained above, it preferably is removable there from so that the system can be stored separately. "Removable" means that it is not permanently fixed on it but on the contrary: that it is positioned there in a reversible way so that it can be removed from the container and put back again as many times as required and this very easily, without substantial effort and without damaging anything.

According to the invention, the container and the bag have no hole or other relief matching at least part of the driver or of a connecting piece between the driver and the mixing device. In other words: there is no mechanical engagement whatsoever between the driver and the mixing device.

By doing so, there is no need to provide the bag and the container with an opening or other relief for communication purposes, no need to manufacture an additional connecting piece so that the container is standard and can be used for any purpose.

In a preferred embodiment, which is quite simple, the mixing device is merely lying/fixed on the bottom of the bag which merely rests on a plane part of the container. Hence, in that embodiment, a portion of the flexible bag is sandwiched between at least a portion of the mixing device and a portion of the rigid container, these portions being generally part of the bottom wall of the bag and of the rigid container respectively. "Sandwiched" means that said portions are directly in contact and pressed against each other by gravity (if the mixing device rests on the bottom of the mixing bag and the container) and/or by any other means which preferably do not perforate the bag and the container (additional magnets for instance).

According to the first embodiment of the invention, the mixing device and the driver are located very precisely relative to the rigid container. In that embodiment, preferably, the mixing device is secured to the bag; and the alignment facilitating device comprises means for positioning the driver at a precise location relative to the device.

Preferably, the mixing device is securely fixed to one of the bag's walls, preferably to its bottom wall or a side wall, preferably in a place close to the bottom. It may be fixed there by welding or by mechanical coupling (welding, clipping . . . ) with drain(s) or other part(s) fixed into the bag. It is preferably welded to the flexible bag by at least part of its bottom (if it has one) or by a basement disc if it has no bottom (preferred embodiment described earlier). This basement disc can merely be a prolongation of the wall of the mixing device.

The welding of the mixing device to the bag (the case being) is preferably performed using common industrial devices like heat impulse welding devices which work by pressing against each other the layers to be welded together using heating stamps. The level of pressure and pressure uniformity are relevant for obtaining a good sealing. The welding temperature and the width of the welding zone are also relevant thereto. Accordingly, all these parameters should be optimized for each practical case. It is worth noting that the same welding technique is generally used to manufacture the bag by assembling the above mentioned films (walls of the bag) and to weld the mixing device therein.

Alternatively to welding, the precise positioning may be obtained through at least one of the following:
  magnets in extension arms susceptible to work with corresponding magnets disposed in the rigid container;
  at least two extension arms welded (or mechanically fixed in any other way) to at least two drains or two other rigid components of the bag.

In this "precise location" embodiment, the flexible bag is received in the container in a way such that the mixing device always occupies the same location relative to it, which means that its centre should be aligned with a given point of the container with preferably only up to 1 mm possible offset. This point generally is substantially the centre of the bottom of the container.

This precise location can be achieved by adapting the tolerances of the outer size of the bag and the inner size of the container and/or by fixing the bag by at least one of its accessories (for instance a drain) at a fixed location of the container. Inserting at least two of the bag drains through two matching holes in the container and securing them there gives good results. In fact, all the rigid parts present on the bag could be used to attach the bag precisely into the container. Hence, instead of drains, sampling ports, inlet/outlet ports, the external tubing of a sparger system . . . could be used.

In this embodiment, the driver must also be located very precisely relative to the rigid container, which means that it must also always occupy the same location relative to it, with the same definition as above. In order not to loose magnetic forces and hence, torque transmission, said driver is preferably at least partially in contact with the rigid container, preferably at least in the zone where the magnet(s) are located.

The precise location of the driver relative to the rigid container can be achieved by making this driver specific to the container i.e. non removable.

However, as explained above, in order to limit the number of drivers (expensive parts) for a given park of containers, the driver is preferably removable. Accordingly, the container is preferably provided (directly or indirectly, via an intermediate part like a frame for instance) with guiding means insuring that the driver will be located at the same place each time it will be fixed on the container. Depending on the kind of guiding means and their location, the driver could be fixed directly (through direct manual action) on the container or the intermediate part, or it could be assisted by a trolley, roller plate or the like.

Guiding means allowing direct manual fixation would be for instance any frame, open compartment or other support fixed underneath the container (or on a part where the container is resting like a roller plate or simply: the floor), which is within the reach of an operator and in which the driver can be firmly secured at a precise location. To that end, clips, locking castors or pins cooperating with matching holes, or the like could be used.

They could also consist in four fixation parts able to receive and fix the arms of a shaft bearing the driver and which an operator could slide underneath the container until the end of the arms are in their fixation part. He could even eventually assist manually the fixation if required (for instance by inserting a pin through matching holes).

Finally, they could consist in a kind of drawer underneath the bottom of the container, said drawer comprising blocking means to keep the driver at a given location therein. Provided the drawer is completed closed by the operator, the driver inside of it can be located very precisely relative to the container in that way too.

Alternatively to direct manual fixation, a trolley, roller plate or the like (which will be called "trolley" further on for sake of simplicity) may be used in conjunction with guiding means to move said trolley and bring the driver at its precise location. There, the driver could be fixed automatically (for instance by using locking castors) or it could be fixed manually (if the fixation points are within the reach of an operator). Also, the driver could be fixed alone (or on a support) on the container and the trolley removed thereafter. Alternatively, the trolley could remain on the container and help fixing the driver there.

In a first embodiment, the guiding means for the trolley are directly fixed to the rigid container. They may comprise at least one rail in which the trolley is first engaged and then moved (for instance using a wheeled cart or trolley) to a precise location where it will be fixed (like in the above cited WO 2006/002091 application). This rail may be able to cooperate with at least one roller or wheel (preferably at least two) located at one end of the trolley. The other end of the trolley may be provided with a cross member (or any other hanging means) allowing to fix said trolley (with the driver on it) to the container.

In a second embodiment, the guiding means for the trolley can be part of an intermediate support structure on which the container rests. This intermediate support structure may be a roller plate used to move the container around; it may also be an intermediate frame inserted in between said roller plate and the container. The latter is preferred because it allows using existing containers and their roller plates.

This embodiment also may use rail(s)) which is/are then integrated to the intermediate support. This support preferably has fixations (like hollow upstanding extensions) compatible with the feet of standard containers (so that said container may merely be rested on said frame by its feet). It may also comprise a chamber or other protection shield for tubing security (i.e. for preventing tubing extending from the bag from touching the floor underneath the tank).

As described in the above mentioned prior art document (WO 2006/002091), the rail(s) mentioned above may be straight. However, if the bottom of the container comprises a small beam extending downwards at its periphery (i.e. if the bottom is supported on a frame), it would be required to first roll the trolley underneath the fixation location and then, to lift completely the driver before fixing it. Hence, preferably, said rail(s) is/are inclined in which case the trolley will be lifted progressively while its wheel(s) are climbing the rail(s). When it reaches the end of the rail(s), its lower extremity can be lifted up for bringing the driver in contact with the container bottom.

In that embodiment, the trolley is preferably equipped on one end with at least one wheel (preferably 2 wheels) resting on the floor when the trolley is not hang up on the container; somewhere in between both ends, with at least one foldable foot bearing a wheel which rests on the floor when the trolley is disengaged from the rails and which folds back when the trolley is engaged with the container and starts climbing the rail(s); and on the other end, with at least one wheel (preferably 2 wheels) which roll(s) on the rail(s) when the foldable foot is folded back.

Once the driver has been correctly located or preferably, at the end of said location process, it is being fixed to the container or to the intermediate frame by any suitable means. These means may comprise locking castors located at one end of the rail and able to cooperate with corresponding holes in the trolley in order to automatically fix the trolley at the end of the rails when it arrives at that location. In this embodiment, the trolley is preferably equipped with a hanging device (for instance, hooks matching with the shape of the beam of the container) so that when the operator feels that the locking castors have engaged with the holes, he merely has to engage these means.

For solving the problem of going beneath a peripheral beam of the container, an alternative to the inclined rail could be to provide the trolley and the container with means allowing the driver and/or at least part of the trolley (the one bearing the driver) to move up and down so that it can retract (get closer to the floor) while passing the beam and lift up again after having passed the beam.

These means might be electrical (like a small elevator for instance) or purely mechanical (like dashpot(s) or spring(s) on the driver and/or trolley cooperating with a deflector on the container).

Another alternative for solving the "beam" problem could be to remove a part from the frame so that it acquires substantially the shape of a "U" and that the trolley can be rolled underneath the container by the open end of said "U".

All these solution may of course be used in combination.

A feature which is preferably present in all the above mentioned embodiments is the fact of putting the driver on a support provided with means allowing said driver to be pushed against the bottom of the container while allowing it to move a little vertically in order to be able to address the problem of the deformation of the bottom owed to fatigue and of other reasons for non flatness of said bottom (for instance if it is angled or convex). Dashpots, springs and the like can be used for that purpose. Alternatively, the support itself may be flexible (either by its nature (if it is made of rubber for instance) and/or by its dimensions).

Hence, the present application also concerns a locating system as described above and allowing the location of a driver below a rigid container, as close as possible to its bottom and in a place where the container has no hole or other relief matching at least part of the driver or of a connecting piece between the driver and the mixing device, said bottom being not necessarily flat.

This locating system comprises means for guiding the driver to said location and for fixing it there, together with a support allowing to fix the driver in said location, said support comprising means for pushing the driver against the bottom of the container in a place where the container has no hole or other relief matching at least part of the driver or of a connecting piece between the driver and the mixing device.

In one embodiment, the support of the driver comprises means allowing it to move a little vertically relatively to the container so that non flat bottoms can be dealt with.

In another embodiment, to solve the same problem, the support itself is flexible.

In yet another embodiment, the locating system comprises at least one inclined rail adapted to be fixed to a standard rigid container (directly or through an intermediate support) and a trolley suitable to support a magnetic driver and to be engaged at least partly under the container when bearing said driver, the trolley comprising:

a body with two ends suitable for supporting the driver;
at one end of the body, at least one wheel intended to roll on the floor;
at least one foldable foot bearing a wheel which rolls on the floor when the trolley is disengaged from the container and which folds back when the trolley is engaged with the container; and
at the other end of the body, at least one wheel which never contacts the floor but which rolls on the rail when the trolley is engaged with the container.

At the end close to the wheel rolling on the floor, the trolley preferably comprises a handle in order to be able to move it easily. At the same end, it also preferably comprises hanging means for hanging said end to the container in order to put and keep the driver at its right location, pushed against the bottom of the container. These hanging means may have the shape of hooks collaborating with springs.

Preferably, the inclined rail is part of an intermediate frame as described above.

The materials used for all the above described equipment are preferably able to withstand sanitization and the wheels of the trolleys are preferably "pharma" compliant. Said trolleys preferably include the control unit of the driver and all electrical wiring thereof. All metals preferably are submitted to passivation in order to obtain the surface smoothness required (and the absence of staining plus ease of cleaning associated).

In the second embodiment mentioned above, rather than fixing/securing the mixing device to the bag tightly and fixing the driver firmly to the container (or to an intermediate support structure fixed to it), the mixing device and the driver are free to auto align themselves through the magnetic forces they exert on each other. This can be achieved by giving at least one of these devices a degree of freedom i.e. allowing it to make small displacements in at least one direction of space (but preferably two, or even three) so that it can move through the magnetic forces between both elements and align itself with the other one. Preferably, it is the mixing device which is allowed to move.

In order to allow the mixing device to move, the flexible bag may comprise a "free" positioning mechanism to position and maintain the mixing device only approximately at a given location (i.e. said device is not secured to its walls but free to move a little relative to it) when the bag is inserted inside the rigid container (but without the mixing device being coupled with the driver of course because then, the location is precise through self alignment). This "free" positioning mechanism may include welding tabs, bridges or any other fixation part (like a double annular wall for instance) fixed on the bag wherein the mixing device is retained but can move freely (relative to the bag) in at least one direction of space (and preferably, in the three directions of space) while remaining in a given perimeter (surrounding the driver when the bag is inserted in the rigid container).

Preferably, in this embodiment, the alignment facilitating device comprises means for allowing the mixing device to move relative to the bag while remaining in a given perimeter thereof so that when the bag is located proximate to the driver, the mixing device will align itself with the driver.

This is advantageous because the mixing device will align itself automatically with its driver (through the magnetic forces they both exert on each other) so that there is no need for a perfect location of the driver on the rigid container. This embodiment is also advantageous because there is no need for the welding of a (potentially) large circumferential part, what present quality issues as far as leakages are concerned.

This embodiment allows decreasing constrains on the manufacturing of both:

the flexible bag by avoiding all the different parts needed for the precise relative positioning of the turbine inside the bag the stainless steal parts, mainly by avoiding precision on the relative positioning of the magnetic driver on the trolley, and on the relative positioning of the trolley versus the container and this for the several designs of container—driver—trolley—intermediate frame (or not) disclosed above for the "precise location" version. Hence, the same hardware (driver locating system) may be used for both solutions although precision/tolerances may be a little less constraining in the case of the "free" version.

In a second aspect, the present invention concerns a flexible bag equipped with a liquid substance circulation device, a particular device of that kind and a liquid substance circulation system.

The mixing and/or suspension of solutions is required in many technical fields such as biotechnology, pharmaceuticals and medical. Liquid substance circulation devices are particularly useful for the mixing of one or more liquid, gaseous or solid substances in the presence of a liquid substance.

There exists a requirement in industry and in research units for a liquid substance circulation device which is effective and inexpensive. This is because all the existing devices have various drawbacks as explained in more detail below for the particular fields that the invention tends to target.

For example, in the field of the biotechnology industry, it is often necessary to prepare and to complement solutions, buffers, culture medium, suspensions, etc (referred to in general terms hereinafter as liquid substances).

More specifically, in the field of biotechnology, some specific applications of circulation devices include dilution, dissolution and/or adjusting pH, salinity conditions, concentration, osmolality, temperature, of a liquid substance of any kind (buffer, culture medium, saline solution, etc.)

Many devices are known for circulating a liquid substance ranging from the simple magnetic stir bar designed to stir a solution in a beaker, for example when preparing said solution, to appreciably more sophisticated devices involving the circulation of the liquid substance by an industrial pump, etc.

To be safe and effective for their intended use, solutions of culture media, buffers, reagents, etc. used in these fields must be pure and sterile. Accordingly, the mixing tank, mixing device, and all other reusable components that contact the solution must be carefully cleaned after use to avoid any cross contamination with subsequent batches of solutions. The cleaning of the structural components is labour-intensive, time-consuming, and costly.

In order to avoid these cleaning steps, single use "mixing bags" have been developed. These are disposable flexible bags provided with a stirrer and intended to be supported in a rigid container. Advantageously, as disclosed in U.S. Pat. No. 3,647,397, the stirrer can be a magnetic stirrer (and more particularly a magnetic stir bar) and is driven by an external driver positioned outside of the bag and may be part of or fixed to the rigid container. By doing so, there is no risk of contamination of the contents of the bag from the outside. However, because the magnetic stir bar is simply disposed on a bottom surface of the bag, it has the propensity to decouple and, perhaps, fly off from the magnetic hold of the external driver, particularly at high rotation rates, and it also has the tendency to wear off said bottom surface by friction.

Several inventions have attempted to address this issue. For example, U.S. Pat. No. 7,153,021 discloses one such a container system with a mixing dish assembly that holds a magnetic stir bar. The magnetic stir bar, when engaged with an external drive, rotates in the mixing dish which is welded to the edge of an opening in the bottom of the flexible bag. The mixing dish, with its "substantially frustoconical side wall" and its welded position below the bottom surface of the bag acts to maintain the stir bar in position. The mixing dish is preferably disclosed as being provided with a retention plate for the stir bar and comprising several openings for putting the inside of the mixing dish in liquid communication with the inside of the bag.

Another prior art attempt to address the issue of securing a magnetic stir bar at the bottom of a flexible container is disclosed in US 2004/0062140. This publication discloses a "rod containment disk" that is disposed on the bottom of a flexible container to contain a magnetic rod or stir bar and prevent its exiting the magnetic field formed by the external driver. The rod containment disk includes an upper ring and a lower ring connected together with bolts and including spacer posts to allow enough room for the stir bar to rotate.

While such prior art devices succeed in some manner to retain the stir bar, they have limited mixing efficiency due to the resulting undirected and non-uniform liquid flow in the bag. Even if the mixing efficiency of such systems is somewhat increased due to the presence of the retention devices which allow higher bar rotation speeds than classical systems, such systems bring about a turbulent agitation of the liquid substance. The turbulent agitation of the liquid substance creates rotation of the liquid substance thereby creating several dead zones.

Because, in the first prior art publication, the retention plate comprises simple drain-like openings (holes) across most of its surface and, in the second prior art publication, the openings formed in the upper ring and between the spacer posts are large compared with the surface area of the containment disk material, fluid exchange between the dish/rod containment disk cavity and the inside of the bag is disorganized and random, the openings allowing the liquid to flow in both directions depending upon the mixing conditions.

Indeed for the preparation of a liquid substance, when the volume is large, a magnetic stir bar alone does not afford homogenization of the solution, because, as from a certain volume, it is generally considered that the magnetic bar puts the liquid substance in rotation without homogenizing it. Even in smaller volumes, devices that use magnetic agitators tend to put the substance into rotation rather than distributing the substances to be mixed in a manner that achieves uniform, quick and efficient mixing. Such reduced homogenization leads generally to unmixed zones and to inaccurate conditions within the liquid substance, since a parameter measured over time does not really reflect the exact value of the parameter of the prepared liquid substance.

It is therefore an object of the invention to address these drawbacks by providing a flexible mixing bag with a liquid substance circulation (hereinafter "mixing") device that provides uniform and efficient circulation (mixing) of the liquid substance by avoiding global rotation of the substance and by reducing the presence of dead zones when mixing one or more liquid substances and/or one or more solid substances in the presence of a liquid substance.

The present invention also aims to provide a mixing device, adaptable to any type of containers designed to contain a liquid substance to be homogenized, maintained in suspension, prepared or even for culturing cells or microorganisms, not requiring any investment with regard to equipment and which is inexpensive.

The bag and device according to the invention is also inexpensive by affording a considerable saving in time during the preparation of the liquid substance, homogenization, maintaining is suspension.

The bag and device according to the invention can therefore be considered as being designed to be disposable if it is so wished in order to avoid any cross contamination.

Moreover, the liquid substance circulation (mixing) device according to the invention ensures a real mixing by circulating and homogenizing the liquid substance and does not bring the liquid substance in turbulent movement or in rotation which would unavoidably result in several dead zones.

The present invention aims at providing a flexible bag equipped with a very efficient liquid substance circulation (mixing) device. This problem is solved by using a liquid substance circulation (mixing) device based on the principal of a centrifugal pump (i.e. with liquid flow organization) which can be magnetically driven from the outside (with a magnetic driver) and which is able to accumulate (build up) sufficient pressure in order to maximize the action area of the device.

Accordingly, the present invention relates to a flexible mixing bag equipped with a liquid substance circulation (mixing) device comprising a rotary magnetic element located in a compartment delimited by a wall, said mixing device further comprising:

at least one liquid inlet located in the central area of the wall; and at least one liquid outlet located in a peripheral area of the wall.

According to the invention, the terms "flexible bag" designate a bag or pouch made of walls of similar structure preferably assembled by welding. These walls may be made of a mono- or multilayer film including a barrier layer based on a barrier polymer like EVOH (ethylene vinyl alcohol polymer). Generally, these films may have an inner layer (in contact with the contents of the bag when filled) based on a polyolefin, preferably an ULDPE (ultra-low density polyethylene, pref. medical grade).

The bag may be of cylindrical shape although cylindrical flexible bags are not easily baffled and difficult to manufacture. A bag with a cubic or parallel-piped shape is preferable namely because it works as a baffled tank.

The flexible bag according to the present invention is equipped with a liquid substance circulation (mixing) device and is therefore referred to as a mixing bag. The mixing device preferably includes sidewall portions with or forming one or more outlets, the side wall portions including deflector portions positioned and shaped to deflect liquid substance as it exits the outlets.

The terms "equipped with a mixing device" mean that the bag contains a mixing device inside the space defined by its walls or communicating with said space. This mixing device may be fixed to one of its walls, preferably to the bottom wall or a side wall, preferably in a place close to the bottom. It may be fixed there by welding or by mechanical coupling (welding, clipping . . . ) with drain(s) or other part(s) fixed into the bag. If may for instance be fixed by welding its periphery (or a specific flange provided therefore) to the periphery of an opening into the bag.

When the mixing device is welded on an opening of the bag, its bottom may be provided with at least one portion in relief (generally a cavity) matching a corresponding portion in relief (generally a protrusion) on a driver (generally part of/fixed on a rigid container supporting the bag, said driver being a magnetic one able of driving the rotary magnetic element) or on a rigid container used to handle the flexible bag. These complementary portions in relief enable to align mixing device and driver very easily. It is namely preferable that the rotary magnetic element is well located upon the driver for optimum torque transmission, avoiding decoupling and avoiding wear concentration (good balance of the element around its rotation axis).

The welding of the mixing device to the bag (the case being) is preferably performed using common industrial devices like heat impulse welding devices which work by pressing against each other the layers to be welded together using heating stamps. The level of pressure and pressure uniformity are relevant for obtaining a good sealing. The welding temperature and the width of the welding zone are also relevant thereto. Accordingly, all these parameters should be optimized for each practical case. It is worth noting that the same welding technique is generally used to manufacture the bag by assembling the above mentioned films (walls of the bag) and to weld the mixing device therein.

In an alternative embodiment, rather than the mixing device being fixed/secured to the tank walls, the bag may comprise a positioning mechanism to position and maintain the mixing device at a given location when the bag is inserted inside a rigid container equipped with a magnetic driver able to drive the rotary magnetic element, the mixing device being merely located inside the bag without being secured to its walls. The positioning mechanism mentioned above may be at least one of the following:

magnets in extension arms susceptible to work with corresponding magnets disposed in the rigid container;

at least 2 extension arms welded (or mechanically fixed in any other way) to at least 2 drains or 2 other rigid components of the bag;

welding tabs, bridges or any other fixation part (like a double annular wall for instance) fixed on the bag wherein the mixing device is retained but can move freely (relative to the bag) in at least 1 direction of space (and preferably, in the 3 directions of space) while remaining in a given perimeter (surrounding the driver when the bag is inserted in the rigid container).

This embodiment is advantageous because the mixing device will align itself automatically with its driver (through the magnetic forces they both exert on each other) so that there is no need for a perfect location of the driver on the rigid container and that a single, non sophisticated driver can easily be used for several rigid containers. This embodiment is also advantageous because there is no need for the welding of a (potentially) large circumferential part, what present quality issues as far as leakages are concerned.

According to the invention, the mixing device comprises a compartment delimited by a wall. This wall may be a continuous surface without angles like a bell which would be fixed to or lie on a bag wall by the open end thereof. It could also be maintained in tabs, bridges or inside a double annular wall allowing it to move freely a few millimetres in at least one direction of space (as explained above). In that embodiment, the rotational axis of the magnetic element (if there is one: see below) may be fixed to the top of the bell so that there is no bottom surface needed.

Alternatively, said wall may be a kind of box comprising different walls defining angles between each other and/or comprising a cover and side walls which may be welded and/or otherwise assembled to each other (for instance by a snap fit system). It may also comprise a bottom surface although this is not mandatory if there is no rotation axis for the rotary element or if said axis is fixed to the cover (top of the wall).

In any event, the surface (wall) being continuous or not, rounded or with angles, it is preferred that the height (H) and the diameter (D) of the compartment (provided it has a circular section, which is preferred) is such that it has a H/D ratio of less than 0.5 and even more preferably of less than 0.3. If said compartment comprises a dome (or raised ceiling), mixing will be less efficient due to the lessened pressure build up capacity.

In a preferred embodiment, the height of the compartment leaves enough space in height for the rotating element to rotate freely but not too much space however in order to allow sufficient pressure build up (which will be explained later on). It is also worth noting that having all height occupied by the rotating element could also increase too much said pressure and increase risk of leakage (in the case of a welded mixer) and decoupling of the rotary element. A good compromise is obtained when the rotary magnetic element occupies at least ¼ of the height between the bottom and the top the compartment (substantially in the centre of both), preferably at least ⅓ of said height. Preferably, it does not occupy more than 90% of said height and even more preferably, not more than 75% thereof.

Another design factor that has an influence on the performance of the mixing device is the ratio between the rotary element length and the compartment diameter. The ratio is preferably at least 0.5 and preferably at least 0.75 and even at least 0.90.

The wall(s) of the mixing device are preferably made of plastic and even more preferably, made of a plastic compatible with the contents of the bag and their use (e.g., a medical grade of a chemically resistant polymer like HDPE). Preferably, this plastic is rigid in order to allow pressure build up without deformation. If the mixing device is to be welded to the bag, the parts of the wall(s) that must be welded on it are preferably of a material compatible with it. Considering the layout of the industrial films set forth above, a polymer of ethylene is a good choice. Preferably, a HDPE (high density polyethylene) is used because other polymers like EVA (Ethylene Vinyl Acetate copolymer) or LDPE are not rigid enough.

The rotary magnetic element comprised in the mixing device according to the invention may be a simple magnetic stir bar rotating on the bottom of the compartment (if it has one, or on the bottom of the bag in the case of a bell embodiment for instance). However, preferably (in order to avoid friction and hence, provide optimum torque transmission between the element and its driver), this element is a magnetic impeller that rotates around a central axis which is either fixed on/part of the bottom of the compartment (in the case it has one) or of the top thereof. This axis may comprise two separate pins extending from a ring (as disclosed in U.S. Pat. No. 4,162,855, the content of which is incorporated by reference in the present application). Alternatively, it may be a single axis passing through a hole in the rotary magnetic element. More details on this variant are given below, in relation with a specific embodiment of the invention. These details apply to the invention in its broadest scope as well.

Instead of being in the shape of a bar, the rotary magnetic element may have the shape of an impeller having at least 3 arms which may be straight or curved (although this may not allow rotation in both directions) or may comprise curved portions. They may also have sections in the shape of parallelograms. The rotary magnetic element may also be in the shape of a cross (or plus sign). The rotary magnetic element may also have the shape of a disc in which magnet(s) are embedded symmetrically versus the rotation axis. This disc preferably wears an upper relief in the form of paddles which are preferably straight (not curved) so that the disc can rotate in both directions.

Whatever the shape of the rotary magnetic element, its decoupling from its rotation axis (at high rotation speed or during shipping and handling) can be avoided by providing adequate securing means on the axis. The securing means may be an adequate relief of the end of the axis (such as a cross shaped portion for instance, the axis being inserted in the hole of the element by its other extremity). The securing means may also be a plug (blocking plate with fixation means) fixed on top of the axis after said axis has been inserted into the hole of the rotary element.

As will be described in more details later on, if the rotational axis is a physical one, it preferably comprises a protrusion from the bottom of the mixing device or of the bag (if the mixing device has no bottom) or from the top of the mixer, said protrusion being equipped with a bearing which fits in a corresponding hole of the rotary magnetic element. In that embodiment, the protrusion preferably comprises embossings (generally in the number of 3 or 6, 6 being preferred) or has the shape of a cross to provide a tension plugging and a perfect fitting between protrusion and bearing and to block rotation of said bearing.

In the mixing device of the present invention, liquid flow is well organized i.e. the liquid enters though specific opening(s) and leaves through other specific opening(s), the former being located centrally and the latter, peripherally. "Specific" means that a given opening only acts as inlet or outlet opening and not as both. The terms "central" and "peripheral" are to be construed as being complementary i.e. "peripheral" means decentralized.

According to the invention, the mixing device comprises at least one inlet opening and at least one outlet opening. Preferably, there are at least two outlet openings and even more preferably, at least four or even, up to six if the container to be mixed has big dimensions. When there are four, the outflow directions are preferably pointing at the corners of the bag. There are however preferably not more than 8 outlet openings in order to avoid increasing too much the head losses (which would reduce pressure build-up and hence, mixing efficiency). Also, the outlet openings are preferably designed hydrodynamically. This will be discussed more in details later on.

In order to favour pressure build up, the outlet openings are preferably located on the side wall of the mixer. Even more preferably, they occupy 40% or less of said side wall surface area, preferably 30% or less and even more preferably less than 20% of said side wall surface area.

In this embodiment, the wall defining the compartment is discontinuous and preferably comprises a substantially flat top (roof) where there only is/are inlet opening(s) and a side wall where there only are outlet openings. Even more preferably, said side wall is substantially perpendicular to the bottom of the bag.

Also, in this embodiment, the outlet openings preferably are in the shape of vertical slots which extend substantially over the entire height of the side wall. If there is an obstruction on their bottom, solids will not be well agitated on the bottom of the bag near these slots and complete emptying will not be allowed and if there is an obstruction on their top, gas bubbles can accumulate which will tend to render the system unstable and reduce mixing efficiency.

Although the openings through which liquid enters/exits the mixing device are located on the wall(s) of the mixer, this does not exclude the fact that they could be "extended" by tubes (perforated or not), baffles or the like which may extend from the compartment into (and even out of) the bag. What is important is that the mixing device must be able to centrifuge the liquid, i.e., to put the liquid in circulation from a central point of its compartment towards a radial direction by rotating at high speed (for instance a few hundreds of rpm or higher, for instance up to 1000 rpm or higher). Hence, in the case there would be a space between the bottom of the mixing device and the bottom of the bag, the inlet and/or outlet openings could also be located in the bottom wall of the mixer. This may be the case if the mixing device is welded on the bottom of the bag through welding feet (so that it looks like if it were built on piles inside the bag).

Also, it is preferred that the side wall of the mixing device is not continuous but instead, consists of parts of given geometry (slices of an annular wall; parallelograms; triangles; curved halve moons . . . ). This is described with more detail in the frame of a specific embodiment later on. These parts need not be identical nor do they need to be disposed symmetrically versus the rotation axis of the magnetic element, although they preferably are. Preferably, their shape is rounded such that the outlet slots are shaped hydrodynamically. This reduces pressure drop as explained above. In the case the side wall comprises six identical parts separated by six identical slots and is put into a parallel-piped bag, good results (in terms of mixing homogeneity) are obtained when two of said parts are traversed in the middle by the small median of the bag bottom. This is also preferably the case when there are four such parts and associated slots.

In one embodiment, to increase the vertical action distance of the mixer, the height between inlet and outlet openings is increased by fixing a tube of a certain length on the inlet opening. To be compatible with injection moulding, this tube is generally not longer than 10 cm. It is worth noting however that longer flexible tubes for instance obtained by extrusion could be fixed to the central area of the mixer.

The outlet flow directions also characterize the action area of the mixer:
  axial outlet flow (generally through openings in the top of the mixing device wall) generally limits the action area horizontally and doesn't allow homogenization of liquids heavier than water and solid suspensions which tend to accumulate on the bottom; however, it may be required in the case the mixing device is located outside the bag and welded to the periphery of an opening into the bottom of the bag (unless tubes are provided to deflect the liquid radially after it exits the top of the compartment) or if the flexible bag has a height to diameter ratio (H/D) of 2 or more;
  radial outlet flow (generally through openings in the side wall of the mixer) generally limits the action area vertically but allows heavier liquids and solid suspensions to be mixed; hence, radial expulsion with the mixing device being located in the bottom centre of the bag is preferred when the mixing device is located inside the bag but it implies multiple exits in order to cover the entire bottom area.

Preferably, in the device according to the invention, there are several outlet openings and the outlet flow directions are in a plane which is either parallel or perpendicular to the rotational axis of the magnetic element (which may be real or virtual). Preferably, the outflow directions are all parallel to the bottom of the bag, so perpendicular to the rotation axis. This allows a better homogenisation of solids and/or liquids at said bottom.

As mentioned above, pressure build up is a preferred feature of the mixing device according to the invention. Hence, the design of said mixing device is preferably adapted to obtain a pressure inside the compartment of at least 10 mbar, preferably at least 20 mbar and even more preferably, of at least 50 mbar when the rotary magnetic element is rotated at about 1000 rpm (which is a quite classical rotation speed). However, in order to limit the risk of leakage and decoupling of the rotary element, said pressure is preferably not exceeding 500 mbar, even more preferably not exceeding 300 mbar and in some instances, even not exceeding 150 mbar.

In order to limit the vortex effect mentioned previously, it may be advantageous to provide the inlet opening (or the open end of the tube, the case being) with anti-vortex means as will be described below. Alternatively, there could be several inlet openings located in the central area of the wall. The presence of anti-vortex means allows reducing the risk of decoupling of the magnetic rotary element from the driver. The presence of a physical rotation axis where the rotary element is retained also helps reducing this risk.

In one embodiment, the mixing device comprises an opening for bubbling gas inside of it. It then preferably also comprises an internal baffle around the rotating element in order to prevent the gas bubbles from interacting with the liquid flow in that area. This baffle must of course leave some space for the liquid to flow out, in the space between said baffle and the wall of the mixer, to reach the outlet opening(s). Preferably, in order to achieve that, the baffle has a restricted height allowing the liquid to pass over it.

In another embodiment, the bag is provided with baffles external to the mixing device but located close to its outlet openings in order to guide the liquid flow (preferably in several directions) and to promote the homogeneity of the mixing effect. Some of these baffles may be linked to/prolong parts of the mixing device wall.

In yet a further embodiment, the flexible bag comprises at least 2 facing walls and a mixing device located inside of it on one of said walls, the other facing wall comprising a cover having a cavity matching the external shape of the mixing device. This cover is preferably fixed (preferably by welding) on an opening of said wall and more precisely: the lower border of said cover is welded to the outer periphery of said opening i.e. on the outer surface of the bag.

The term "matching" means in fact that the mixing device fits (can be inserted) inside the cover and can be removed there from easily i.e. that the mixing device has smaller dimensions and an adequate shape to be able to be received (preferably completely) inside the cover.

This embodiment prevents the bag from being damaged owed to the presence of a rigid mixing device inside of it. It also allows the mixing device to be kept in place during shipping and handling when said mixing device is not fixed to the bag (see above).

The invention also relates to a liquid substance circulation (mixing) device provided for being placed in a container comprising at least a bottom surface and a rotary magnetic element for rotating around a central axis extending vertically from a bottom plate, being optionally the same as the bottom surface of the container, provided to be driven by a motor external to the container.

The liquid substance circulation (mixing) device according to this embodiment of the invention is characterized in that that said device further comprises a compartment delimited by:
- an upper plate, provided with an inlet in the central area, said bottom plate and
- a peripheral wall extending vertically from the bottom plate and comprising a plurality of side wall portions, each side wall portion being separated from each other side wall portion by an outlet slot, and each outlet slot and each side wall portion being respectively disposed symmetrically to other outlet slots and to the other side wall portion.

The presence of a first compartment with an upper plate comprising a liquid substance inlet in the central area allows the device to axially aspire said liquid substance. The presence of the plurality of outlet slots being each a liquid substance outlet allows the device to radially bring the liquid substance out of the circulation device in a parallel manner with the bottom surface of the container. Therefore, the liquid substance is circulated throughout the container thereby reducing the presence of dead zones. Indeed, the liquid substance is displaced along the bottom of the container and the complete bottom surface of the container is perfectly swept and stirred before being guided by the container wall(s) upwards and being again aspired by the liquid substance inlet.

Moreover, the plurality of outlet slots being each a liquid substance outlet and the fact that each outlet slot and each side wall portion are respectively disposed symmetrically one to each other, acts conjointly to allow the device to accumulate a predetermined pressure without creating a decoupling of the rotary magnetic element, within said compartment. The accumulation of pressure within said compartment creates a sufficient circulation movement of the liquid substance and prevents turbulences in the liquid substance flow due to the alignment of the outlets which also reduce the presence of dead zones. The liquid substance does not rotate, is perfectly swept and presents in any point a relative speed which is different from zero.

Advantageously, the compartment has a substantially circular internal cross section and each side wall portion presents a convex external surface.

The circular internal cross section acts as a first guiding means to exit the liquid substance out of the compartment while the side wall portion presenting a convex external surface acts as a second guiding means. The convex external surface allows the liquid substance to reach the corners of the container and/or the farthest portions of the bottom of the container from the circulation device according to the invention. Therefore, the presence of dead zones is strongly reduced because there is no portion of the container which is not reached by the liquid substance flow exiting the circulation device.

In a particular embodiment, the peripheral wall comprises four side wall portions together defining a quatrefoil circumferential shape.

In this manner, the pressure accumulated in the compartment is particularly optimal and the liquid substance existing the circulation device according to the invention is also particularly well guided by the four external convex shape of the side wall portion.

In a particularly advantageous embodiment according to the invention, the rotary magnetic element comprises a central hole provided for receiving a bearing element provided on a protrusion extending perpendicularly from said bottom plate.

The aforementioned feature (i.e. the physical presence of an axis) allows higher speed for the rotary element. Indeed, in order to reach a sufficient flow rate of the liquid substance when exiting the circulation device according to the invention, it is required to accumulate a sufficient pressure inside the compartment. This pressure sometimes creates a resistance towards the rotation movement of the rotary magnetic element thereby resulting in the decoupling of this latter. The decoupling of the rotary magnetic element will lead to instability, i.e., the rotation speed of the rotary magnetic element can be affected and turbulences can occur. The presence of a central hole for receiving a central axis protruding vertically from the bottom plate counteracts the decoupling, thereby providing a circulation device with higher efficiency by allowing the rotary magnetic element to rotate with higher speed and the accumulated pressure within the compartment become greater, thereby increasing the exiting flow rate of the liquid substance.

In a particularly advantageous embodiment, the central hole is provided for receiving a bearing element provided on a protrusion extending perpendicularly from said bottom plate.

It is of common knowledge that two different parts of a bearing element in friction one to each other should preferably be made of different material. indeed, the rotary magnetic element rotates on the bearing element which is fixed to the bottom plate via the protrusion, i.e. the rotation of the bearing element is prevented, for example with a truncated shape. The presence of the bearing element, being a separate element from the protrusion allows using different materials for the protrusion, for the rotary magnetic element and for the bottom plate.

In a preferred embodiment, the protrusion comprises embossings (preferably three or 6) to provide a tension plugging and a perfect fitting, and the bearing element is engaged in a rotation-free manner on the protrusion by a fixing means.

Preferably, the rotary magnetic element comprises two permanent magnets connected symmetrically at each side of a medium portion, said medium portion comprising said central hole.

This feature enables high rotation speed for the rotary magnetic element without any decoupling of this latter.

In order to produce liquid substances according to manufacturing standards that will allow validation of the liquid substance either vis-à-vis the FDA, or GMP, GLP or other standards, a key feature is to prevent the particle generation due to the friction between the rotary magnetic element and the bearing element.

To this end, in a particularly preferred embodiment, the rotary magnetic element comprises an outer surface of a first polymer having self lubricating properties and being resistant to abrasion and wherein said bearing element is made of a second polymer having good wear resistance properties, said first and second polymers forming a couple having a hard partner and a soft partner.

More particularly, each polymer forming said couple is chosen in the group consisting of polytetrafluoroethylene, polyoxymethylene, high density polyethylene, polyamide, polyetheretherketone and ultra high molecular weight polyethylene and most preferably, the couple of polymers is polyetheretherketone and ultra high molecular weight polyethylene, said polyetheretherketone being the hard partner and said ultra high molecular weight polyethylene being the soft partner.

Advantageously, the liquid substance circulation (mixing) device comprises guiding means upstream of the liquid substance inlet with respect to a liquid substance circulation (mixing) flow, aiming to increase the efficiency of the circulation of the liquid substance. Indeed, due to the presence of the guiding means, for example a tubular body, the liquid substance is aspired in the central area of the container at a higher level, thereby providing a greater circulation movement.

Preferably, the liquid substance circulation (mixing) device comprises anti-vortex means, which can be for example a cross shaped four wall construction extending from the central zone, increasing the circulation efficiency of the liquid substance circulation (mixing) device according to the invention. Indeed, when a commonly known stiffing bar rotates in the bottom of a container, a central vortex, due to the suction siphon of the stiffing bar, is created. The vortex is a dead zone in terms of mixing and circulation with undesirable turbulences.

The cross shaped four wall construction extending from the central zone break down the vortex thereby increasing the efficiency of the homogenization and of the circulation of the liquid substance.

In a particular embodiment according to the invention, the liquid substance circulation (mixing) device comprises retention means provided to lock the rotary magnetic element during shipment and/or handling.

The retention means can be for example, a protrusion extending downwards from the upper plate, from the anti-vortex means or from the guiding means. The retention means can present a cross, a circular, a square shaped cross section, etc.

Advantageously, in a preferred embodiment, the compartment further comprises an inlet provided for bringing a fluid into said compartment. The fluid can be a gas, for example, in order to allow adjusting the gas concentration in the said liquid substance, for example, $O_2$, $CO_2$, $N_2$, etc. This can be particularly advantageous when the liquid substance circulation (mixing) system is used in a cell culture system, for example in a bioreactor or in a pouch or bag or even, when the liquid substance circulation (mixing) device is used in a feeding pouch or bag perfusing a culture of cells or microorganisms in a bioreactor. The fluid can also be a liquid substance being for example a nutriment solution, an antibiotic, a buffer and the like.

In a particularly preferred embodiment, the compartment comprises sensors, in particular optical sensors provided for measuring parameters such as pH, temperature, dissolved oxygen, or existing or future sensor means not requiring direct contact between the probe and the recording means.

In a variant, particularly adapted for cell culture or microorganism culture, the inlet is provided with a filter and/or a membrane preventing the passage of particles or cells, when present.

Advantageously, the rotary magnetic element, having optionally an aerodynamic geometry creates a liquid substance flow rate within the range from 0.6 to 40 litres/min which is particularly adapted for small scale uses.

In a variant, the rotary magnetic element, having optionally an aerodynamic geometry creates a liquid substance flow rate within the range from 10 and 300 litres/min, in particular from 20 to 250 litres/min and preferably from 25 to 200 litres/min, which flow rate is particularly suitable for large scale applications.

Other embodiments of the device according to the invention are mentioned in the annexed claims.

According to the invention, it is intended to manufacture the liquid substance circulation (mixing) device by the following process comprising the steps of:
  injection of the selected polymer, preferably of the high density polyethylene for forming the compartment,
  injection of the selected polymer, preferably of the high density polyethylene for forming the guiding means, optionally comprising the anti-vortex means,
  injection of the selected polymer, preferably of the polyetheretherketone for forming the bearing element of the bearing of the rotary magnetic element, and
  forming the rotary magnetic element with the central hole and both permanent magnets coated with the selected polymer, preferably with ultra high molecular weight polyethylene.

Particularly, the step of forming the rotary magnetic element comprises:
  forming at least two cavities, provided for accommodating each permanent magnet having a predetermined diameter, in a polymer bar having a size close to said predetermined diameter, from each end of the cylindrical polymer bar, said at least two cavities remaining separated from each other by a central part of the polymer bar.
  Machining the central part of the rotary magnetic element for forming said central hole and for giving the outline of said central part,
  inserting each permanent magnet in its own cavity through a terminal end,
  forming at least two covers provided to close each terminal end, and
  welding each cover to the terminal end.

In a variant according to the invention, the step of forming the rotary magnetic element comprises:
  forming at least two cavities, provided for accommodating each permanent magnet having a predetermined diameter, in at least two separate cylindrical polymer bars having a diameter close to said predetermined diameter, each cavity remaining sealed at one end and opened at the other end,
  Machining a polymer bar having a diameter greater than said predetermined for forming a central part of the rotary magnetic element
  inserting each permanent magnet in its own cavity through said open end,
  placing said at least two polymer bars, with their cavities having each its own permanent magnet inside, and the central part in a mold,
  baking said at least two polymer bars together with the central part in a furnace to form a raw rotary magnetic element
  finishing machining of said raw rotary magnetic element to bore the central hole in the central part and to form an horizontal contact area This concept can be generalized to a method for manufacturing a rotary magnetic element, said method comprising the following steps:
  putting at least one polymeric part or powder and at least one magnet into a mould able to mould a rotary element that has or can be provided with (a passage for) a rotational axis in a way such that the magnet(s) are located symmetrically inside the mould versus the axis
  heating the mould to melt the polymer part(s) or powder in order to obtain a single piece rotary magnetic element.

Advantageously, the process according to the invention further comprises a packaging step and a sterilization step, to provide sterile liquid substance circulation (mixing) devices to be used, for example in clinical batch production process.

There exist several applications where it can be appropriate to provide a container provided with a liquid substance circulation (mixing) system.

A first exemplary application is the use of graduated container for the preparation, complementation, dilution or adjustment of liquid substance. Generally, in laboratories, the procedure is to add into the container a stirring bar, preparing, complementing, diluting or adjusting the liquid substance, removing the stirring bar and adjust the volume of the liquid substance to the expected final volume. This leads to inaccurate value, to contamination risk, to a waste of time etc.

For the production of clinical batches or sterile solutions, all steps are carried out in so called "white rooms" and liquid substances to be used should be sterile by autoclaving and/or filtration according to their content which increase the working costs and contamination risk by the technician. For this reason, the use of disposable pouches containing ready-to-use liquid substance has really been increasing. Unfortunately, it is generally needed to adjust the liquid substance by making for example concentration, salinity, pH, osmolality, dissolved gas concentration or/and complementation adjustments. Similarly, it is more and more frequent to harvest or collect media containing molecules of interest (production of proteins, viruses, DNA, antibiotics, metabolites, etc) in such pouches or bags. The harvested or collected media should generally be subjected to further steps requiring homogenization of the content of the pouch or bag.

To solve this problem, the invention encompasses to provide a liquid substance container comprising said liquid circulation device.

For example the liquid substance container can be a graduated container wherein the graduation takes into account the volume of the liquid substance circulation (mixing) device according to the invention. In another example, the liquid substance container containing the liquid substance circulation (mixing) device according to the invention can be an empty pouch or bag designed to harvest a liquid substance from a chemical, biochemical or biotechnological process or can be a pouch or bag containing a basic liquid substance to be adjusted, complemented, diluted, concentrated or even ready-to-use or containing a suspension which should be maintained in movement to prevent sedimentation. This type of container prevents contamination, ensure a sterile container comprising a sterile circulation device, both being provided sterile and ready-to-use, depyrogenated, endotoxin free, etc.

Up to date, some relatively clever devices exist but with their specific drawbacks. For example, ATMI LifeSciences developed the Newmix™ C-MIX system for the preparation of solutions in pouches or bags. The pouches or bags of this type require an infrastructure representing a not insignificant investment for the user and the pouches are very expensive. In addition, this type of device cannot be adapted to other types of receptacle.

In a particularly preferred embodiment, the container according to the invention comprises an amount of solute in the form of powder, aggregates, pellets, granules and the like or in the form of liquid concentrate, or a number of particles to be suspended, and at least one solvent or diluent inlet.

Indeed, it is well known that storage of ready-to-use solutions in a flexible bag or in a rigid container are very expensive in terms of required space. Moreover, the storage period of ready-to-use liquid substance are generally short, resulting in an over-consumption of this latter. The invention intends to provide a sterile container containing the predetermined amount of solute to which only water has to be added. Due to the presence of the circulation device within the container according to the invention, the preparation step of the liquid substance based upon the solute is made considerably easier.

In a particularly useful application of the invention, the liquid substance circulation (mixing) device is used in a culture medium flexible bag or in a medical mixing flexible bag retained in a rigid container.

In the field of cell culture, it is also known to procure sterile pouches containing liquid culture medium often needing complementation (addition of serum, antibiotics, particular nutriments, metabolic markers, etc.) resulting in homogenization and mixing problems, in particular for large scale pouches or bags.

An exemplary system is the WAVE Bioreactor® system which uses a disposable culture device in pouches or bags which presents a problem of circulation of the medium since the pouch or bag undergoes a rocking movement on an agitating plate, which makes it possible to make turbulences in the medium without homogenizing it or making it circulate. Consequently many zones in the pouch are not homogeneous and the cells and/or the cells on carriers sediment and aggregate, which they do not withstand. In addition, for pouches of 500 litres, the agitating plate must be oversized, which means that the mechanical elements of the circulation device of the WAVE Bioreactor® are subjected to high wearing forces and the enormous agitating plate is difficult to design, and is mechanically fragile and very bulky.

Consequently the invention, as mentioned above, sets out to resolve this problem by procuring a liquid substance container comprising a circulation device which can be used for homogenizing culture media in pouches to be complemented without risk of contaminating the culture medium, including for pouches ranging up to 200 or 1,000 litres without involving any additional investment cost, nor any considerable additional cost in use.

In the field of cell culture, some cell culture methods can be carried out within pouches or bags directly. The use of the device according to the invention in culture pouches or bags affords good circulation of the medium and optimum homogenization. Consequently it is possible to cultivate cells in suspension (on carriers or not) in the pouches or bags, since good circulation is achieved, in particular with a filtration membrane at the liquid substance inlet, to avoid cell damages or crushing of cell carriers by the rotary magnetic element.

Finally, the present invention also relates to a mixing device suitable for being used in a flexible bag as described above or in any other type of container, and which is based on the finding that (as already mentioned above) it is advantageous to guide the liquid flow (deviate it from its natural path) when or after it exits the mixing device.

When passing through an opening in the wall of a mixing device with rotary magnetic element, since said wall has a given thickness, the outlet flow undergoes a small local deviation from its natural rotating path and tangential velocity. However, it immediately tends to return to the rotational pattern generated by the centrifugal forces i.e. it becomes again circular (in the case of a cylindrical device) or helicoidal (in the case of a cone shaped device) which limits the mixing efficiency.

One aspect of the present invention aims at solving that problem by providing a mixing device comprising a rotary magnetic element located in a compartment delimited by a wall, said mixing device further comprising:

at least one liquid inlet opening located in a central area of the wall;

at least one liquid outlet opening located in a peripheral area of the wall; and deflecting means that substantially alter the natural rotational direction of the liquid exiting the outlet opening.

The details given previously as to the rotary magnetic element, the materials constituting the wall of the mixing device and the relative dimensions/shape of both do apply to this aspect of the invention.

Pressure build up is also preferably promoted and a shape of the wall such that its inner sections are circular (hence: a cylindrical or an helicoidal shape) are also preferred.

The parameters which are specific to this aspect of the invention are mainly related to the nature, shape and dimension of the deflecting means.

Normally (without deflecting means), when the liquid exits the compartment of the mixing device, its flow path is tangential to the wall of the compartment at the outlet point. The deflecting means of this aspect of the invention act to shift this liquid outflow path from a given angle after the liquid has impacted on the deflecting means so that said flow path tends to become more radial (i.e. the flow direction when the liquid leaves the deflecting means tends to become more parallel to the radial direction at the outlet point). This angle shift is preferably of at least 5°, more preferably of at least 10° and even more preferably of at least 20°. It preferably allows to direct the liquid outflow in any preferred direction, for instance the corners of the parallelepiped-shaped containers in general and flexible bags in particular. These corners are well known to persons of ordinary skill in the art as being dead zones in a mixing process. By this angle shift at each of the deflection means, the global flow pattern created by the mixer within its action area is changed from a circular path to several divergent jets, the number of jets being equal to the number of outlets.

This directional change of the velocity vector occurs directly when said flow leaves (is no longer in contact with) said deflecting means. This permits mixing of the substance away from the mixing device and throughout the bag in a more efficient manner. It allows avoiding dead zones for instances in the corners of the container (bag) to be mixed.

In the mixing device, there are preferably several outlet openings, the number of which depending in fact on the size and shape of the container it is designed for. These outlets are preferably located on a side portion of the wall of the mixer. They are preferably all identical. Advantageously, they are all equipped with deflecting means and even more preferably, with identical deflecting means so that the flow pattern is symmetrical. The terms "equipped with" mean in fact that there are some deflecting means somewhere in the flow leaving the outlet opening but not necessarily directly at said opening.

In the case where the wall of the mixing device is conical, the inlet opening is generally unique and located at the top of the cone while the outlet openings are spread all over it. In the case the wall of the mixing device comprises a top portion (roof) and a side portion (side wall), the latter is preferably vertical and comprises the outlet openings. If the container has a high H/D ratio of at least 2, the mixing device may comprise at least one outlet opening at the top of its wall (roof) but in a peripheral region thereof (and not in the centre). Deflecting means may also be provided at that opening.

According to a first embodiment, the wall of the mixing device has an external surface which, when viewed in radial sections through the outlet opening(s), is not circular and/or comprises portions in relief—a "radial section" being a section through a plane which is perpendicular to the axis of the device and which passes through the outlet opening(s))

This is for instance the case when the mixing device comprises several side wall portions separated by outlet slots and having a convex external surface as described earlier, or even a concave external surface. Other geometries of said portions may also give a deflecting effect for examples if said portions each comprise at least one excrescence.

According to a second embodiment, the wall of the mixing device has an external surface which, when viewed in radial sections through the outlet opening(s), is circular but said wall has a high thickness when compared to the dimensions of the openings so that these act as tubes that guide/deflect the liquid flow. Typically, this is the case when the ratio e/d of said thickness (e) to the diameter (d) of the opening (when viewed in a radial cut i.e. it may be the diameter if the opening is circular or it may be the width in the case of a slot) is at least equal to 1 preferably at least equal to 2 and even to 4. In this embodiment, the higher the ratio, the more the outlet flow pattern will be altered. Generally speaking, the alteration becomes really substantial when said ratio is at least equal to 0.5.

In these 2 first embodiments, the deflecting means are hence formed by the wall of the device itself.

In a third embodiment, the deflecting means are part(s) affixed to or integrated to the external surface of the wall and which may be tubes prolonging the outlet opening(s) or baffles or the like either integrally moulded with said wall or being fixed to it.

In a fourth embodiment, the deflecting means are parts separate from the wall of the mixing device but which are intended to be located somewhere into the outlet flow to deviate its rotational flow pattern. Their size, shape and location are preferably adapted to the size and shape of the container intended to be mixed.

The above described mixing device is particularly useful when used in a flexible bag or rigid container for mixing pharmaceutical solutions and suspensions preferably in a sterile environment.

The present invention also concerns a mixing system comprising a flexible mixing bag as described above; a rigid support for said bag; and a magnetic driver adapted to drive the device in said bag.

Other characteristics and advantages of the two aspects of the invention will appear more clearly in the light of the following description of a particular non-limiting embodiment of the invention, while referring to the figures.

FIGS. 1 to 12 refer to embodiments of the liquid substance circulation device that can be used in the mixing system with both ways of facilitating the alignment, whether the "precise location" or the "free version".

FIGS. 13 and 14 show 2 embodiments of the "free positioning" embodiment of the present invention.

Figure 16:
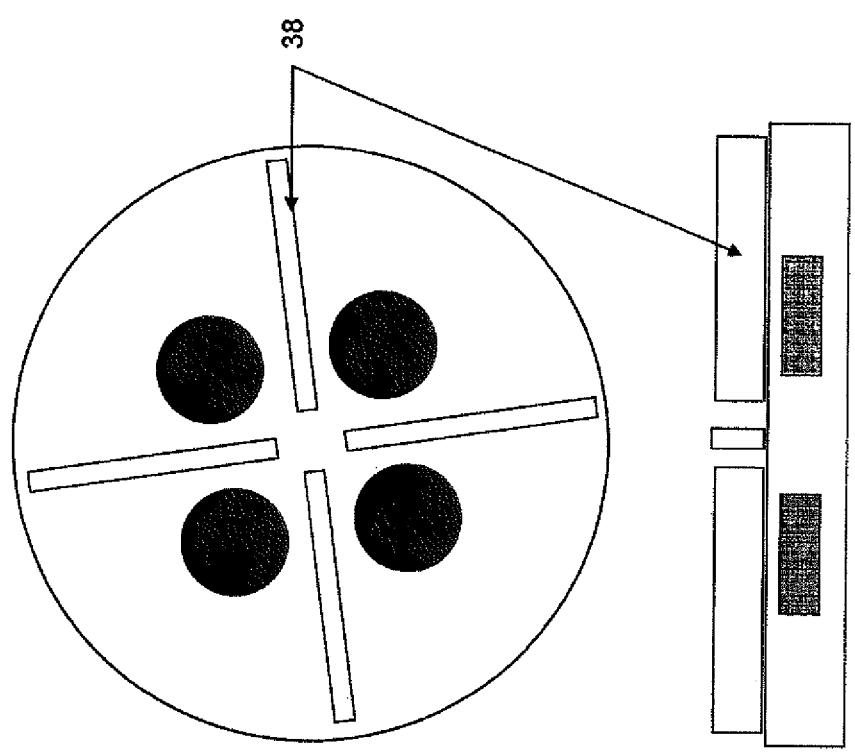

FIGS. 15 and 16 relate to a magnetic impeller with a particular shape.

Figure 17:
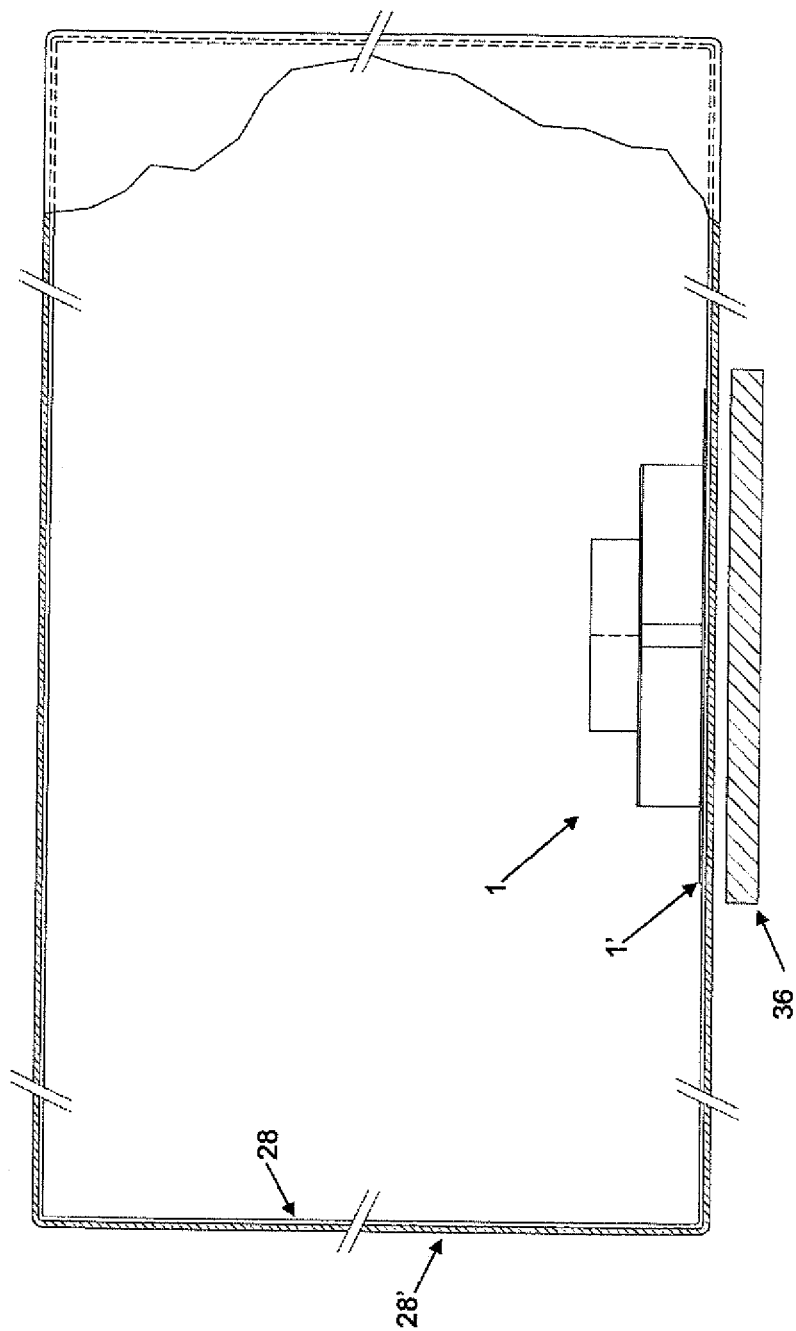

FIG. 17 relates to an embodiment of the invention where the mixing device has no bottom.

FIG. 18 show the shape of some wall portions of the mixing device according to some embodiments of the invention (mixing device with deflective means).

FIG. 19 shows mixing devices with axial output instead of radial (as in the other pictures).

And finally, FIGS. 20 to 24 relate to hardware which is compatible both with the "precise location" and with the "free location" embodiments of the invention.

Figure 20:
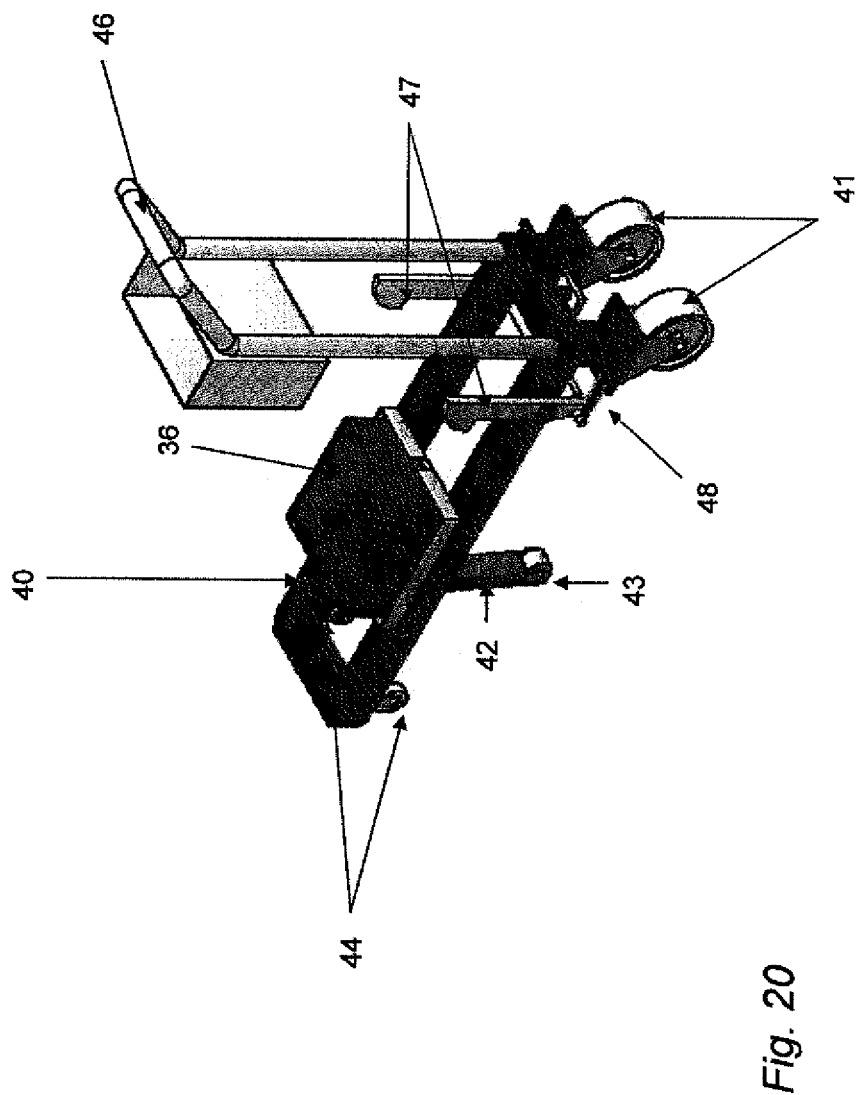
Figure 21:
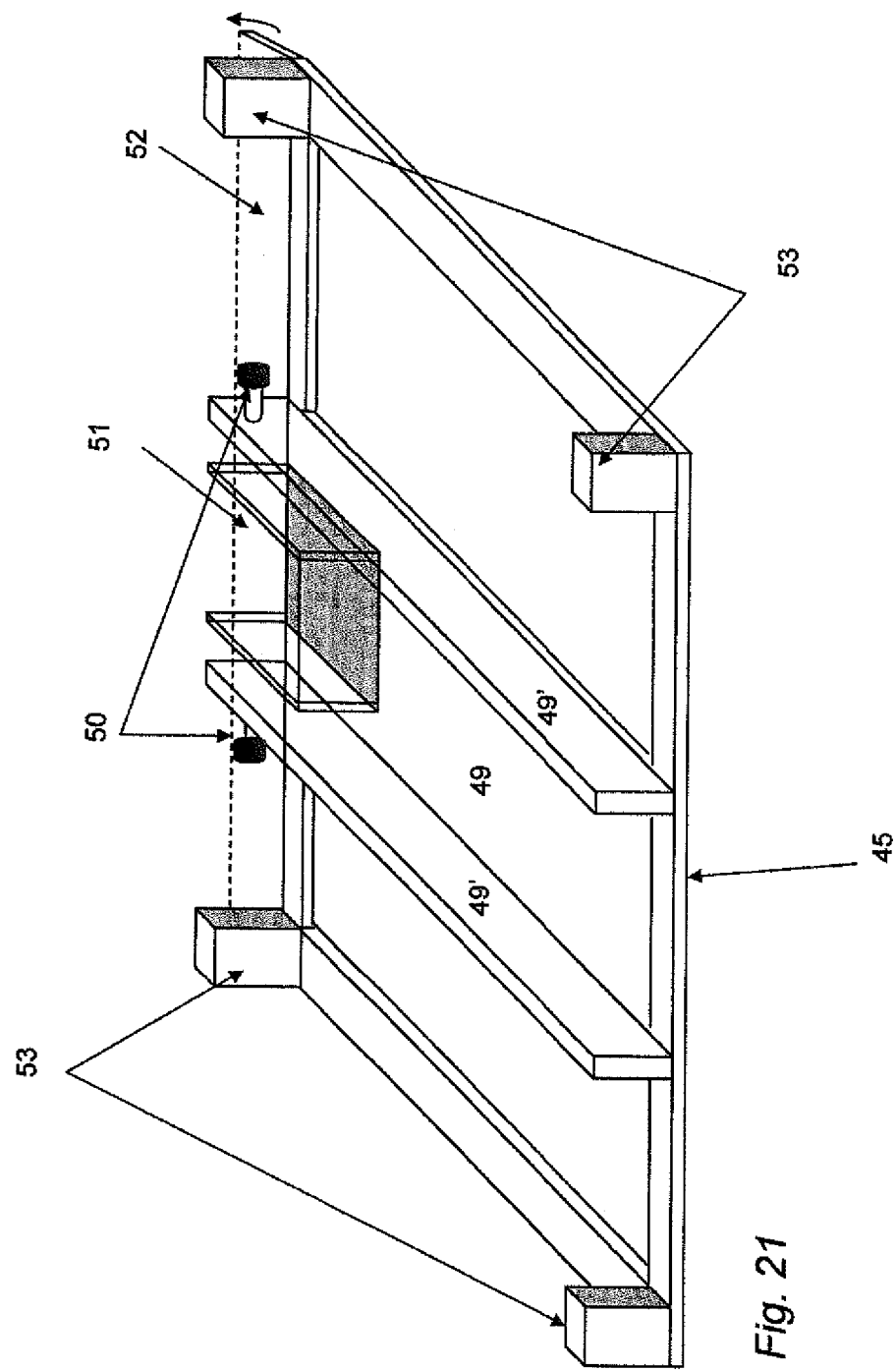
Figure 22:
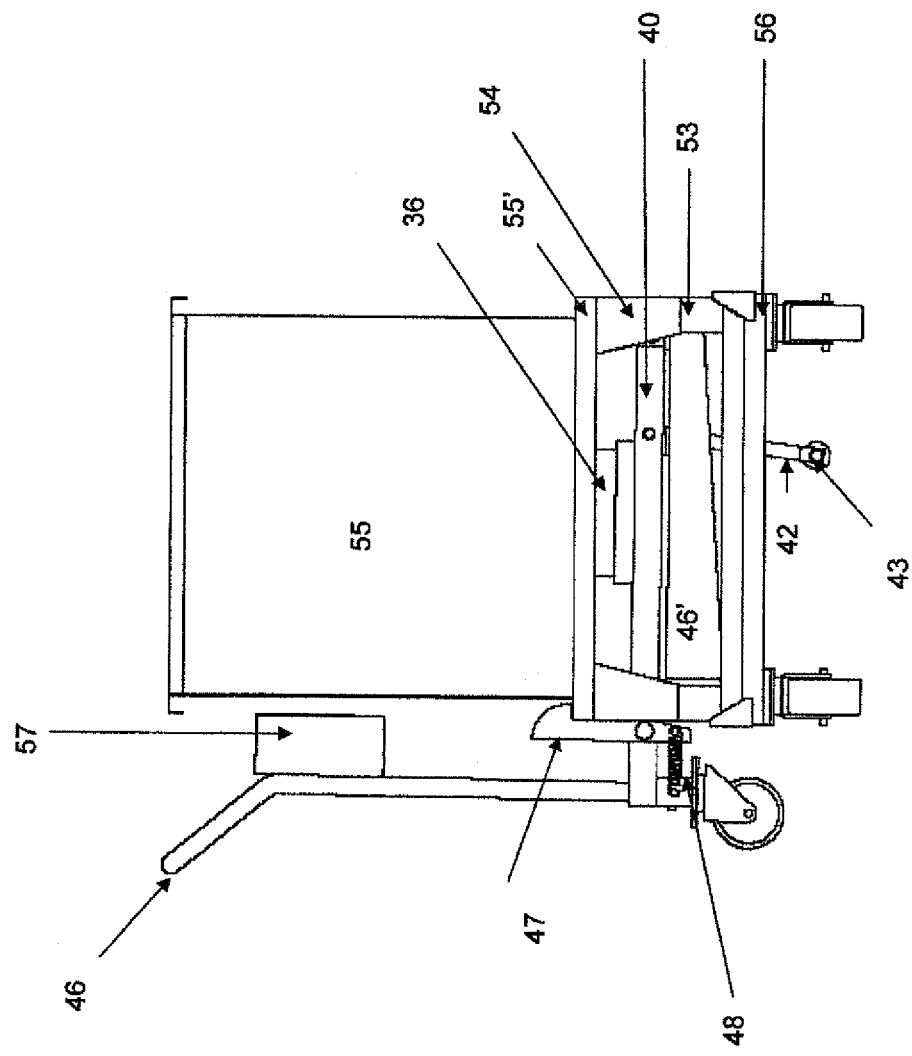
Figure 23:
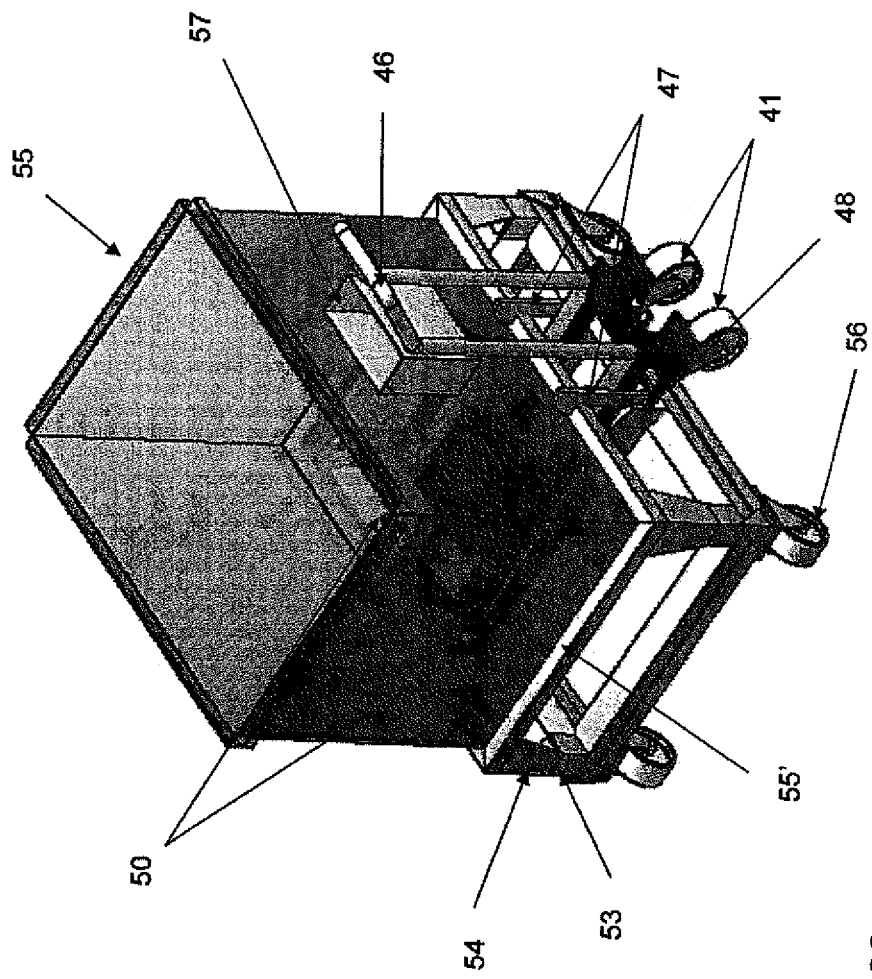

More precisely: FIG. 20 shows a trolley suitable both for the "precise location" version of the present invention and for the "free aligning" version of the present invention. FIG. 21 shows an intermediate frame adapted to work with said trolley and FIGS. 22 and 23 show said trolley and an intermediate frame mounted on a rigid container.

FIG. 24 comprises schematic views of some rigid containers used in the frame of the invention.

In the drawings, the same reference signs have been allotted to the same or analogous elements of the liquid substance circulation (mixing) device according to the invention.

Figure 1A:
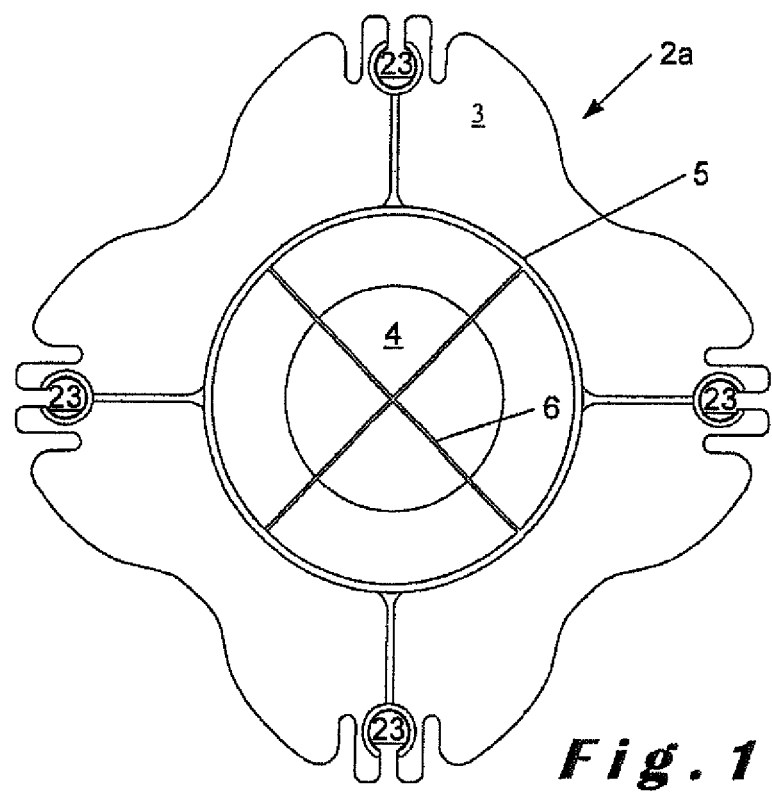
FIG. 1a is a top view of the upper portion of a particularly preferred embodiment of the liquid substance circulation (mixing) device according to the invention.
Figure 1B:
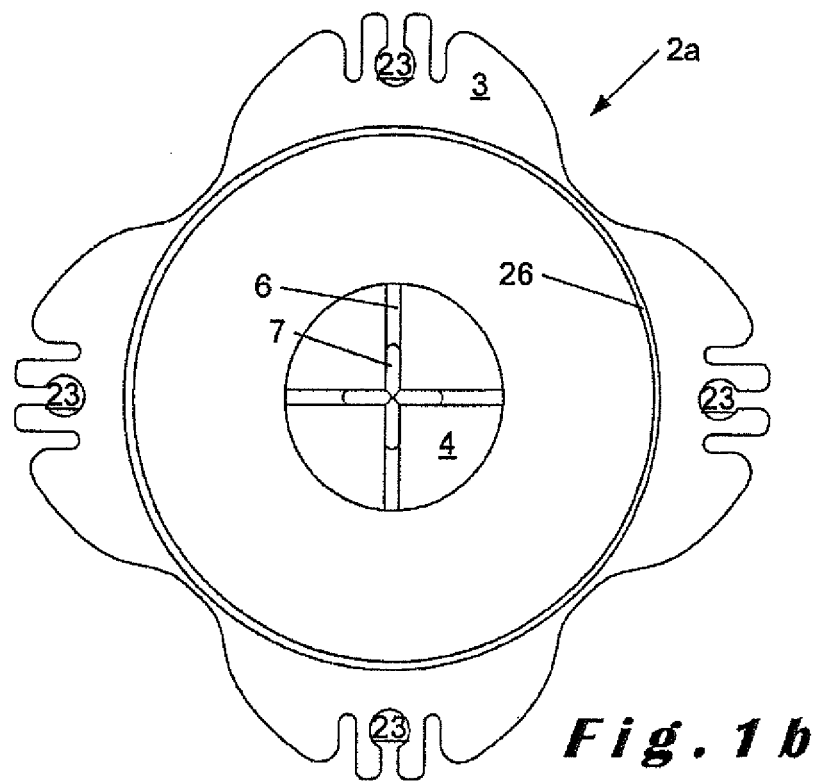
FIG. 1b is a bottom view of the upper portion of a particularly preferred embodiment of the liquid substance circulation (mixing) device according to the invention.

As it can be seen in FIGS. 1a and 1b, the liquid substance circulation (mixing) device 1 comprises an upper portion 2a comprising an upper plate 3 and an inlet 4 in the central area.

According to the illustrated preferred embodiment, the upper portion 2a of the device 1 further comprises guiding means 5 upstream of said inlet 4 in view of the liquid substance circulation (mixing) flow and anti-vortex means 6.

In FIG. 1b, it can be seen that the upper portion 2a of the circulation device comprises retention means 7 for maintaining the rotary magnetic element in place (during transport for example). These means are baffles arranged to form a cross.

Figure 2:
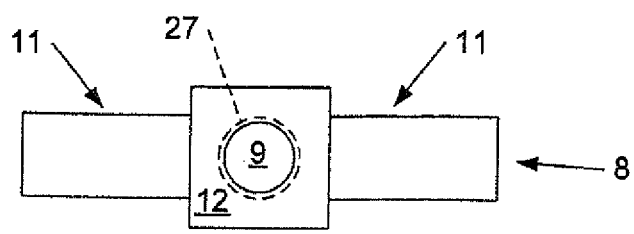
FIG. 2 is a top view of a preferred rotary magnetic element of the liquid substance circulation (mixing) device according to the invention.

FIG. 2 illustrates the rotary magnetic element 8 comprising a central hole 9 provided for receiving a bearing element 10 (see FIG. 3), and two permanent magnets 11 "opposite one to each other" or symmetrically at each side, and connected to a medium portion 12. The medium portion 12 comprises the central hole 9. In some embodiments, the medium portion 12 comprises on its upper surface a recess 27 provided to accommodate the retention means 7 illustrated in FIG. 1b. Indeed, the rotary magnetic element 8 is provided to rotate whilst the upper portion 2a of the device 1, comprising the retention means 7, is provided to be static. It is therefore advantageous to provide a recess 27 avoiding friction strength between the retention means 7 and the rotary magnetic element 8 but maintaining the blocking effect of the retention means 7.

Figure 3:
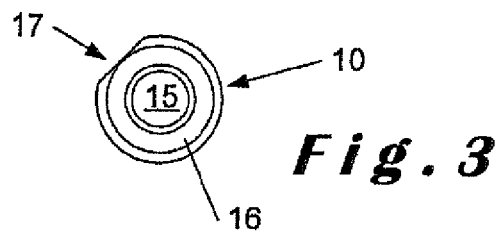
FIG. 3 is a top view of the bearing element of the liquid substance circulation (mixing) device according to the invention.

As it can be seen in FIG. 3, the bearing element 10 being provided for receiving a protrusion 13 (see FIG. 4) extending perpendicularly from said bottom plate 14 within a central cavity 15. The bearing element 10 comprises a bottom surface 16 being not symmetric, for example with a truncated/bevelled region 17, i.e. having an irregular cross section, for preventing the rotation of the bearing element 10 when the rotary magnetic element 8 is rotating.

Figure 4:
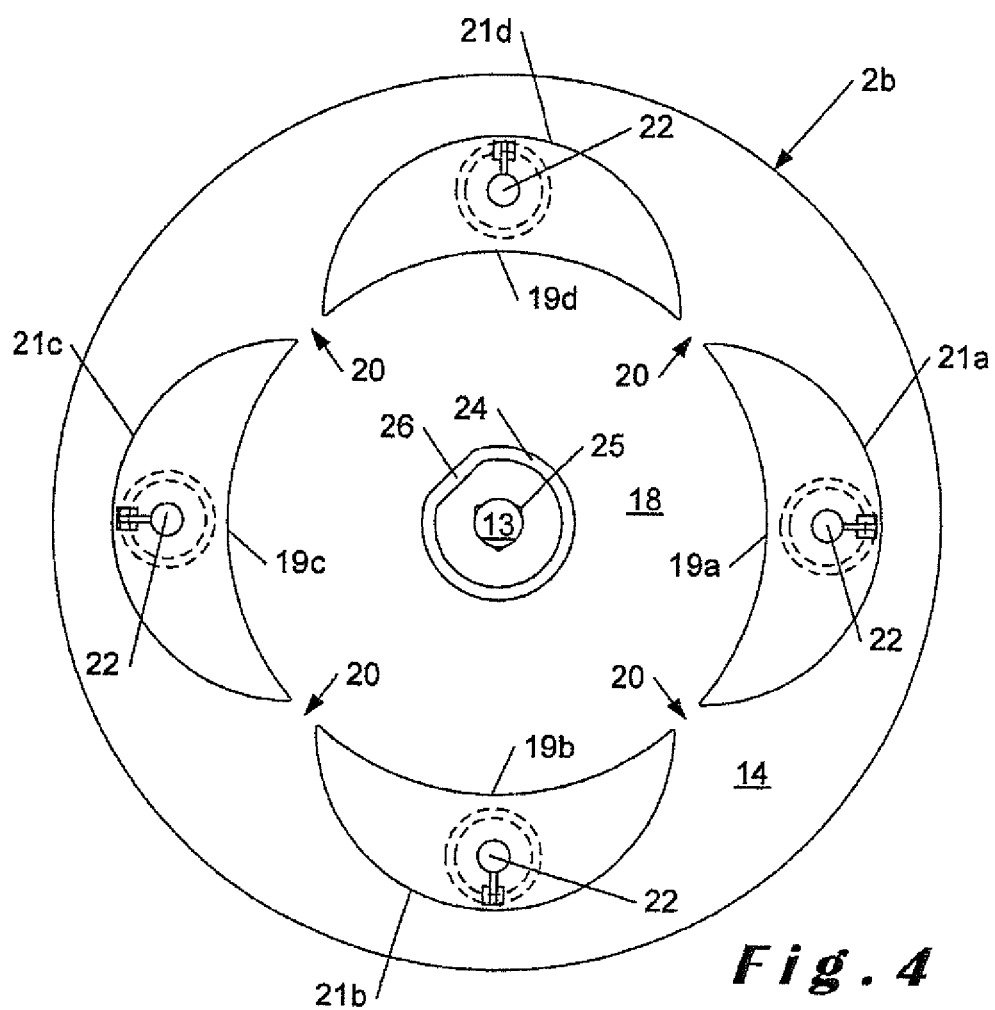
FIG. 4 is a top view of the bottom portion of the liquid substance circulation (mixing) device according to the invention.

FIG. 4 illustrates the bottom portion 2b of the circulation device. The liquid substance circulation (mixing) device comprises a bottom plate 14 (being optionally the same as the bottom surface of the container into which the circulation device according to the invention is intended to be inserted). The liquid substance circulation (mixing) device further comprises a compartment 18 delimited by the upper plate 3 and the inlet in the central area 4 shown in FIG. 1, the bottom plate 14 and a plurality of peripheral side wall portions 19a, 19b, 19c, 19d, etc. extending vertically from the bottom plate 14. Each side wall portion 19a, 19b, 19c, 19d is separated from the other by an outlet slot 20. Each outlet slot 20 and each side wall portion 19a, 19b, 19c, 19d is respectively disposed symmetrically to the others. Preferably, the compartment 18 presents a substantially circular internal cross section and each side wall portion 19a, 19b, 19c, 19d presents a convex external surface 21a, 21b, 21c, 21d.

In the illustrated embodiment, there are four (4) side wall portions together defining a quatrefoil circumferential shape.

The bottom portion further comprises connection means 22, of the "quick connect" type provided to fix the upper portion 2a of the liquid substance circulation (mixing) 1 device to the bottom portion 2b. The upper portion 2a comprises reciprocal connection means 23 provided to accommodate the connection means 22 for fixing the upper 2a and the bottom 2b portions of the liquid circulation device according to the invention. The bottom plate further comprises a cavity 24 with a truncated cross section 26 adapted to receive the bearing element 10 and to prevent the rotation of this latter. Moreover, for a perfect fitting, the protrusion 13 comprises some embossings 25.

Preferably, the rotary magnetic element 8 comprises an outer surface of polyetheretherketone and the bearing element 10 is made of ultra high molecular weight polyethylene, or the opposite. The latter is more preferred (see above).

Figure 5:
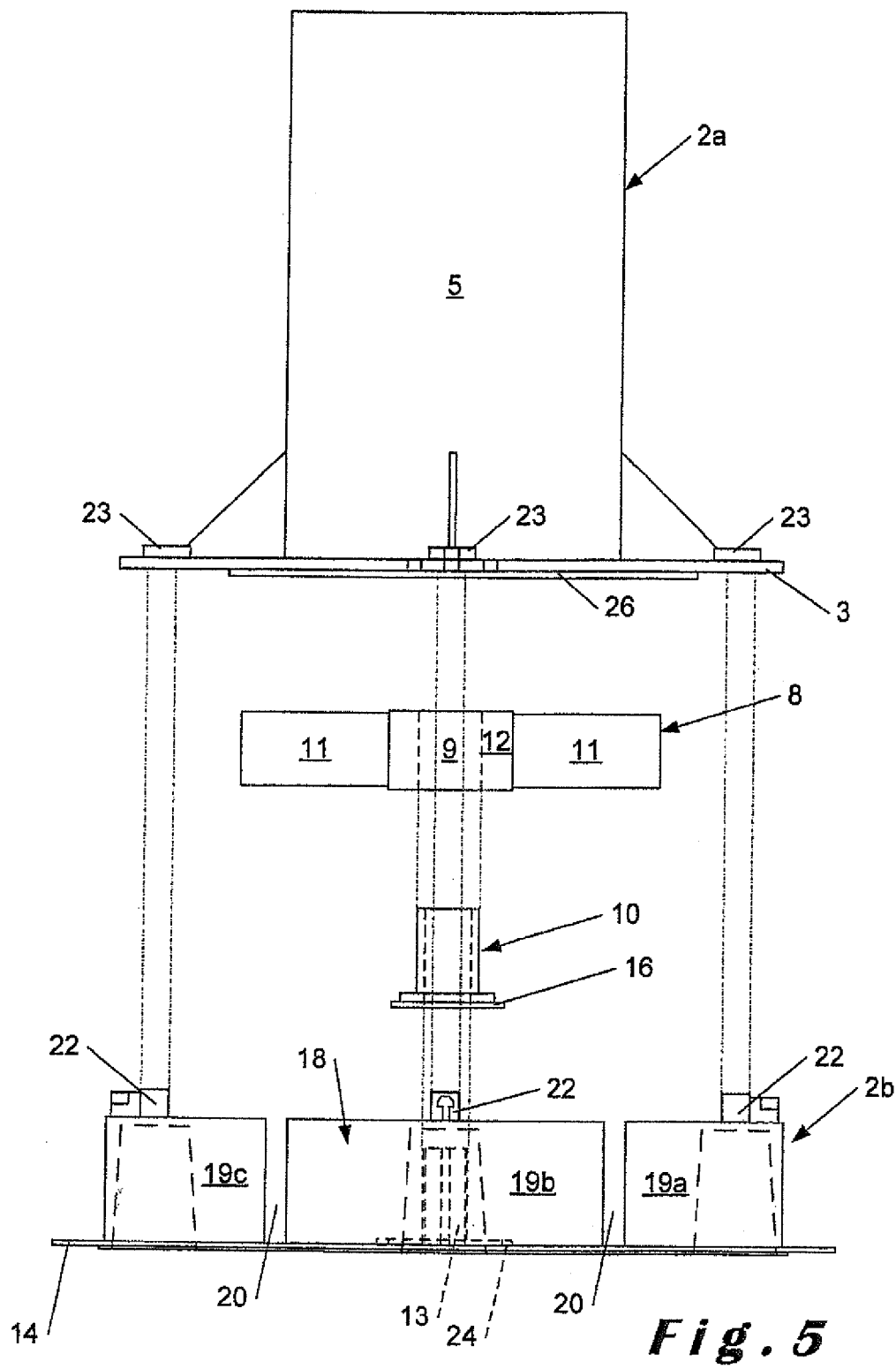
FIG. 5 is an exploded side view of the liquid substance circulation (mixing) device according to the invention.

FIG. 5 is an exploded view of the illustrated device. As can be seen, it is particularly easy to assemble. The bottom portion 2b comprises the bottom plate 14 and the plurality of side wall portions 19a, 19b, 19c, 19d, etc., being each separated from the other by outlet slots 20 delimited a compartment 18, being further delimited by the upper plate 3 of the upper portion. The upper plate comprises a ring 26 provided to be accommodated in the compartment created when the device is assembled.

The bottom plate 16 of the bearing element 10 and the cavity 24 of the bottom plate 14 of the bottom portion 2b present both an irregular cross section (truncated/bevelled region 17 and 26) being the same in order to insert the bottom plate 16 of the bearing element 10 in the cavity 24 of the bottom plate of the bottom portion 2b to prevent the rotation of this latter.

When mounting the illustrated device, the protrusion 13 is inserted into the bearing element 10. The embossings 25 of the protrusion 13 perfectly fit the internal surface of the bearing element 10 to prevent the rotation of this latter.

The rotary magnetic element 8 is then placed around the bearing element 10, this latter being placed in the central hole 9 of the medium portion 12.

After having placed the rotary magnetic element 8 on the bearing element 10, being on its turn, placed on the protrusion 13 of the bottom portion 2b of the device 1, the upper portion 2a has just to be connected to the bottom portion 2b by connecting the connection means 22 to the reciprocal connection means 23.

As can be seen, the embodiment illustrated in FIG. 5 comprises a tubular guiding means 5 upstream of the inlet 4 with respect to a liquid substance circulation flow.

Figure 6:
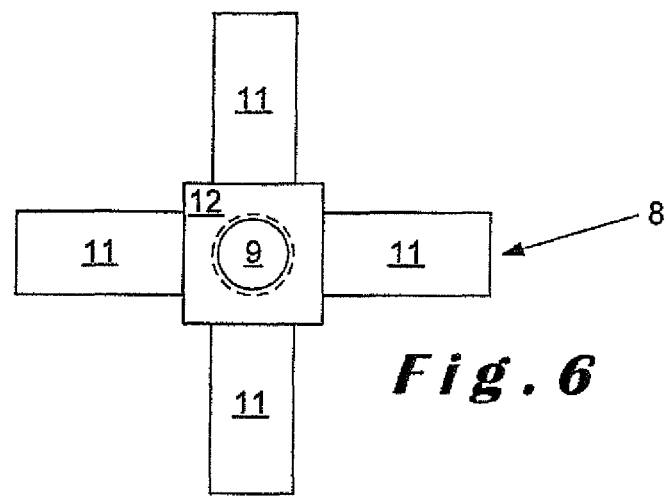
FIG. 6 is a top view of an alternative rotary magnetic element for the liquid substance circulation (mixing) device according to the invention.

FIG. 6 illustrates an alternative embodiment of the rotary magnetic element 8 having a cross shaped cross section. According to the invention, the rotary magnetic element 8 can present optionally an aerodynamic geometry and could create a liquid substance flow rate within the range from 0.6 to 40 litres/min for small scale process and within the range from 10 and 300 litres/min, in particular from 20 to 250 litres/min and preferably from 25 to 200 litres/min, for large scale application.

Figure 7:
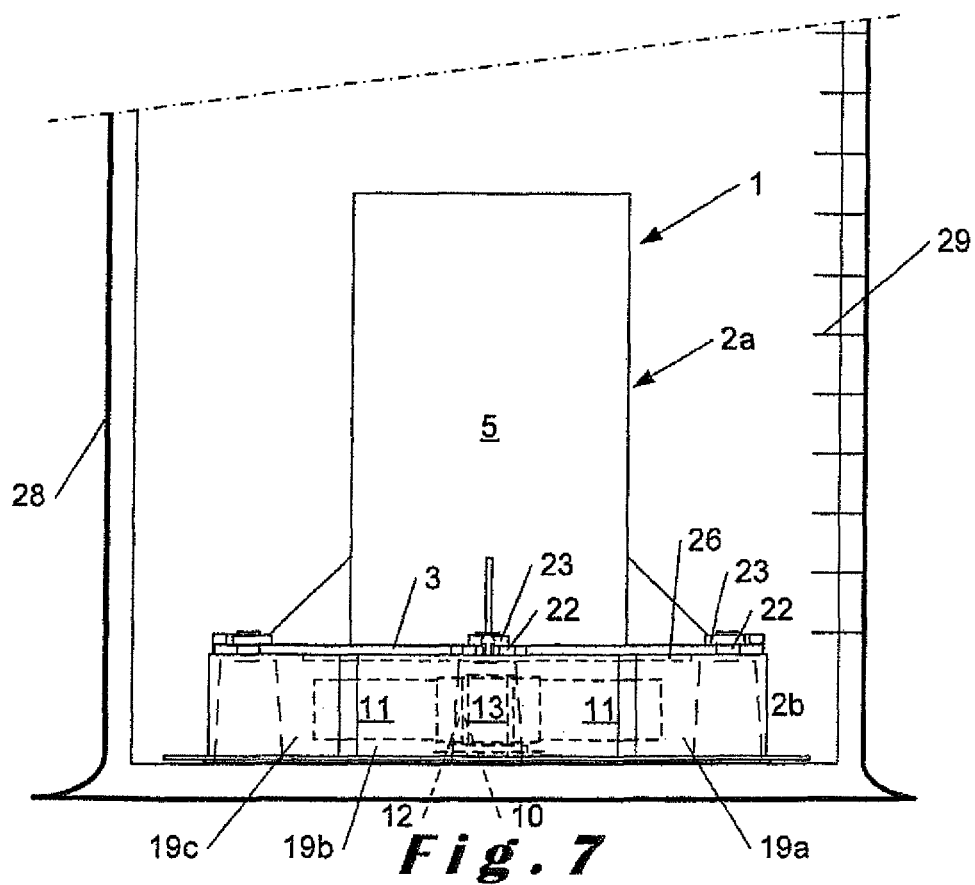
FIG. 7 is a view illustrating the liquid substance circulation (mixing) device integrated in a graduated rigid container.
Figure 8:
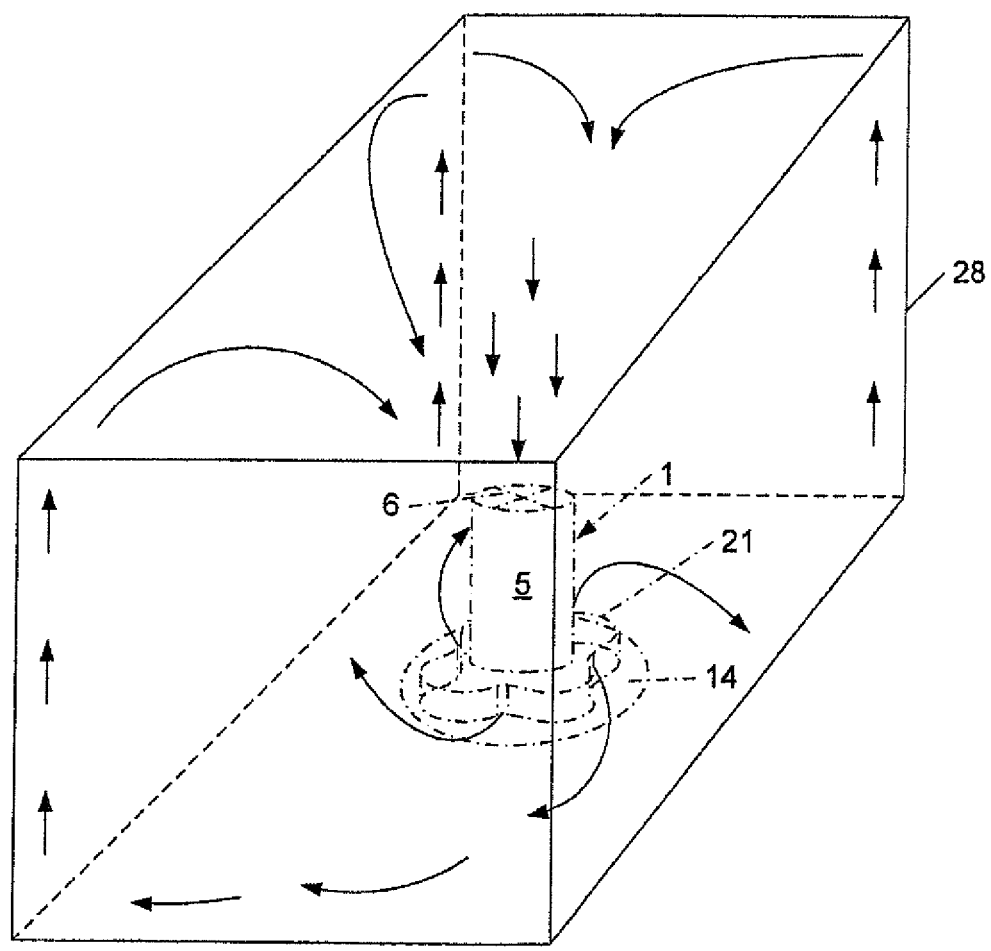
FIG. 8 is a perspective view of the liquid substance circulation (mixing) device integrated in a prismatic container, such as a parallelepiped (flexible bag or pouch of rigid container).

FIGS. 7 and 8 illustrate preferred applications of the liquid circulating device according to the invention.

According to the invention, provision is made for packaging liquid substance circulation (mixing) device 1 in a sterile individual package or supplying it in a non-sterile and packaged form or even non-sterile and non-packaged form. The non-sterile circulation device 1 remains a device for single usage if required, but it can also be reusable, if the users wish to wash and reuse it.

In a particular embodiment of the invention, provision is also made for the liquid substance circulation (mixing) device according to the invention to be autoclaved with a view to its reuse. Consequently, the circulation device 1 according to the invention is designed to be used in normally used containers 28 such as solution storage CARBOYS® or parallelepiped bags 28 (see FIG. 8), or in solution or suspension preparation receptacles 28 (see FIG. 7).

It suffices, if it is packaged individually and sterile, to immerse the liquid substance circulation (mixing) device 1 in the receptacle 28 containing the solution or suspension to be prepared and then to actuate the stator part (driver) in order to set the rotative magnetic element 8 in rotation. According to the invention, the container 28 may be a container 28 supplied with the liquid substance circulation (mixing) device according to the invention which is directly welded in the bottom thereof. In the embodiment illustrated, bottom portion 2b comprises a bottom plate 14 but, when the container 28 is directly supplied with the liquid substance circulation (mixing) device, the bottom plate 14 of the liquid substance circulation (mixing) device 1 can be the same as the bottom surface of the container 28. In addition, when the container 28 is either designed to be used conjointly with the circulation device with a particular fluid, or directly supplied with the circulation device, provision is made for the graduation 29 to directly take account of the volume of the circulation device according to the invention. In the first case, this makes it possible to use the disposable circulation device 1 and to use a new one at each use without having to remove it before the solution is made up to the mark.

Of course, due to the increased sweeping operation of the circulation device according to the invention, when such a container, for example a graduated container is used to prepare a solution, the preparation time is considerably preserved and the quality of the solution is improved. Indeed, when the device is used to prepare a buffer, the acid or base concentration is important with respect to the buffer capacity of the solution and to the concentration to reach (saline conditions, etc.).

When preparing a buffer solution with a device which brings the solution in rotation, i.e. with just a common stirred bar, pH adjustment is really time consuming and it very often occurs that too much acid or base is added because the measured value of the pH is not the exact one that the solution presents. This is because the solution is not immediately homogenous and this drawback generally leads to a varying concentration due to acidic and base addition, reacting together to create a salt modifying the osmolarity and osmolality and even the concentration of the buffer solution. This is also prejudicial to the reproduction of experiments. According to the invention, the rotary magnetic element in rotation creates a liquid substance suction siphon in the said central area and expels the liquid substance sucked radially and tangentially along the external surface of the guiding means, which leads to a nearly perfect instant homogeneity.

Figure 9:
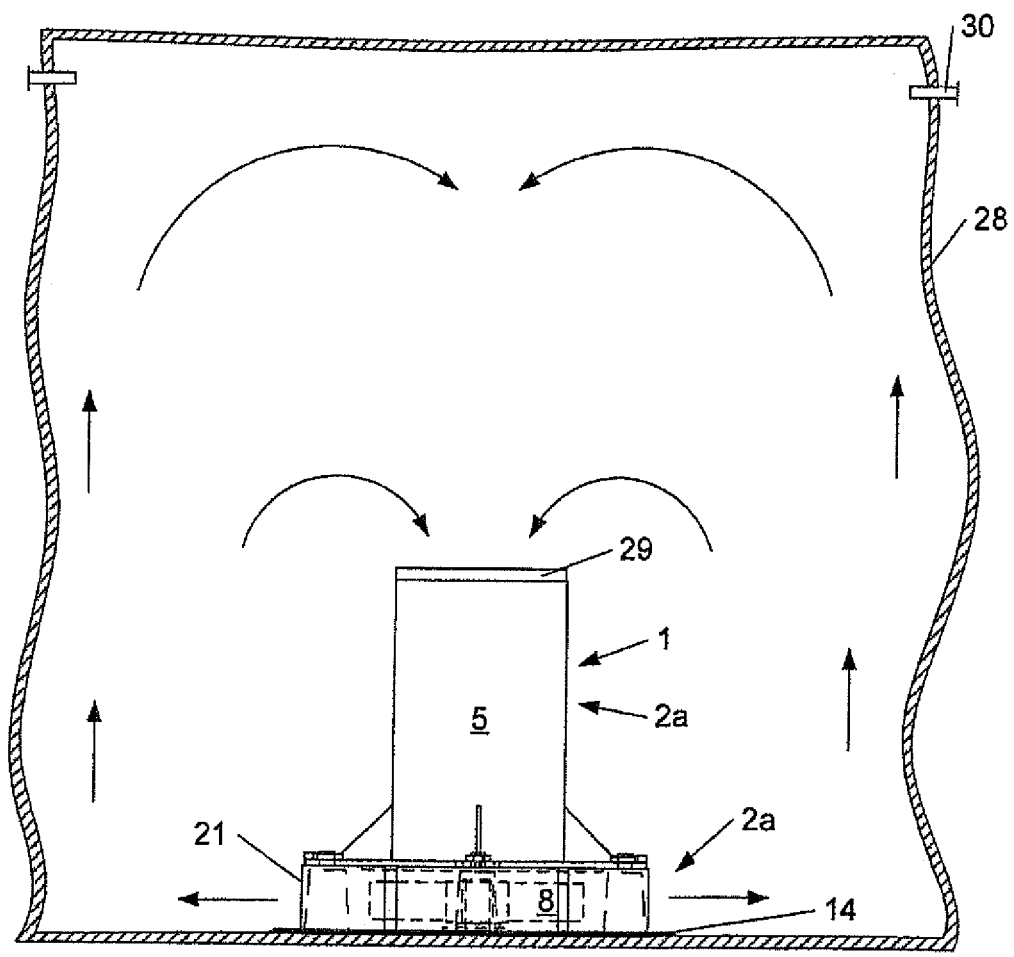
FIG. 9 is a view illustrating the liquid substance circulation (mixing) device integrated in a flexible container such as a pouch or a bag.

FIG. 9 is a schematic view of the liquid substance circulation (mixing) device 1 used in pouch or bag 28, for example to cultivate cells or to produce a solution or a suspension in a close system. In the field of cell culture, the cells can be cultivated on (micro)carriers, in suspension or in a fixed bed. The cells on (micro)carriers or not, both in suspension can be circulated by the device according to the invention. Preferably, in those kind of applications, a filter or a membrane 29 is present upstream the liquid substance inlet or upstream the tubular guiding means 5 if present with respect to a liquid circulation flow (see arrows) for confining the cells in the pouch or bag being a culture vessel 28. The confinement of the cells is advantageous to prevent them to enter into the liquid substance circulation (mixing) device 1 in order to avoid imposing excessively high stresses on them or preventing blockage of the rotary magnetic element 8. In the case of a reactor or a container 28 for producing a suspension of particles, aggregates, powder, granules, etc., it is advantageous to place this type of filter or membrane 29 in order to prevent the particles in suspension in the liquid substance entering the liquid substance circulation (mixing) device according to the invention.

In the illustrated embodiment, the pouch or bag 28 may be used as a culture device or as a medium reservoir for another device. In the case of a culture device of the culture pouch type, the liquid substance circulation (mixing) device 1 according to the invention is used for stirring the culture medium. In the case of a medium reservoir, since generally the packaged medium commercially available in pouches or bags does not comprise the required additives, the device 1 according to the invention may be used for homogenizing the medium contained in the pouch or bag 28 and the additives added via a feeding connection 30. It is advantageous for the circulation device 1 to be directly integrated in the pouch or bag 28 at the time of manufacture. The presence of this liquid substance circulation (mixing) device ensures stirring of the medium and cells by the circulation of the medium within the culture pouch with a perfect sweeping of this latter.

The liquid substance circulation (mixing) device 1 according to the invention makes it possible to use an appreciably smaller driving system requiring less mechanism than the devices generally provided for mobilizing the culture medium in this type of culture devices, such as the tilting stirring plate of the WAVE® system. Consequently the liquid substance circulation (mixing) device 1 according to the invention is much less expensive than those generally used for culture pouches or bags 28.

In addition, since the driving system is practically identical for all the liquid substance circulation (mixing) devices 1, it is also advantageous at this level since only the investment of a single driving system and several liquid substance circulation (mixing) devices 1 is to be made, whatever the diverse applications required. The liquid substance circulation (mixing) device 1 is intended to be produced as a disposable device, and therefore at low cost for enabling its single-use. When the liquid substance circulation (mixing) device 1 is integrated in the container 28, its use make more easier the preparation of solution, suspension, culture and the like because it is provided within the container. The container 28 and the circulation device 1 being both sterile and intended for a single-use. Moreover, for container 28 provided with a solute amount which can be any one of said solute, the user has just to place the container 28 (being rigid, a pouch, a flexible bag or the like) upon the driving system, to connect a feeding tube on the one side to the water reservoir or feeding reservoir and on the other side to a connection 30 provided on the container.

Figure 10:
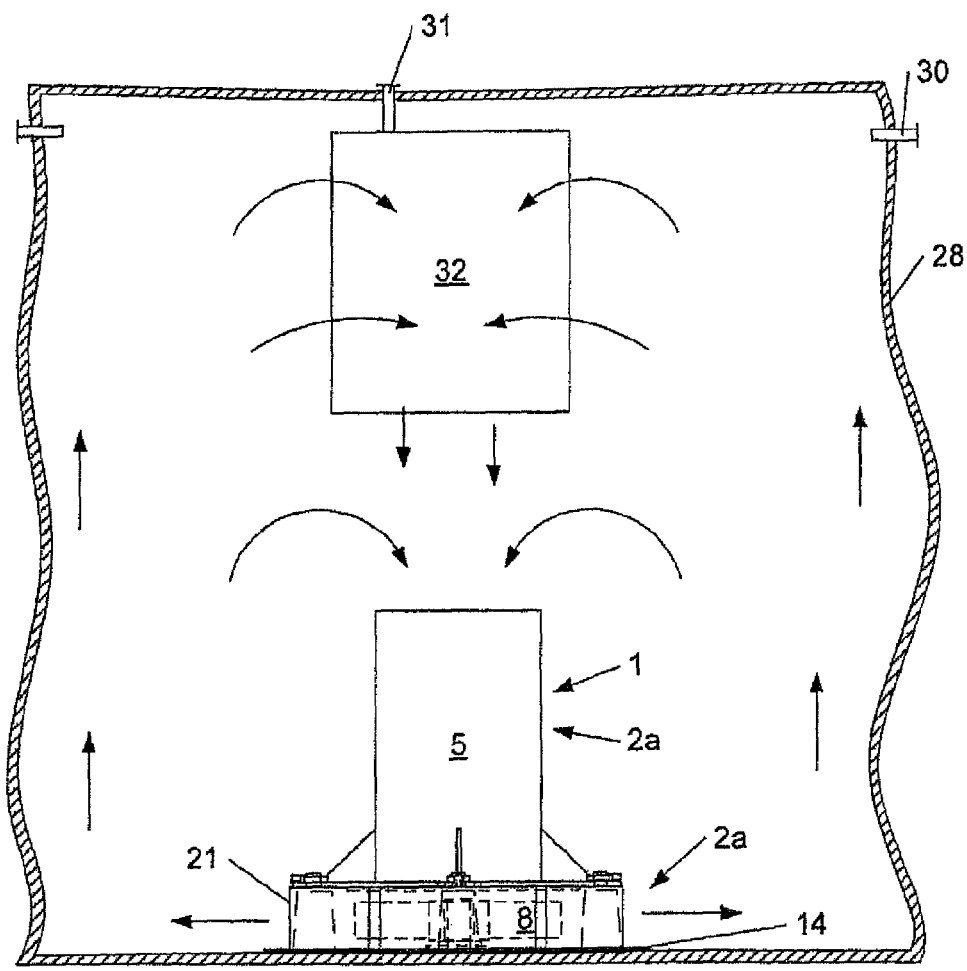
FIG. 10 is a view illustrating the liquid substance circulation (mixing) device integrated in a flexible container such as a pouch or a bag and comprising an internal reservoir.

As can be seen in FIG. 10, it can be advantageous that the flexible bag or pouch 28 comprises a reservoir 32.

In other applications, for example dialysis of a protein in a buffer A against a buffer B, it is advantageous for the container 28 to comprise an internal reservoir 32 comprising one part consisting of a dialysis membrane having a suitable pore size according to the size of the protein to be dialyzed. The internal reservoir 32 of the container 28 according to the invention must retain the protein to be dialyzed but not the buffer A. Consequently, in this type of application, it is advantageous to procure, at the internal reservoir 32, a supplementary addition tube 31 in order to be able to place the sample to be dialyzed in the internal reservoir. Since the homogenization of the liquid substance is maximum and the liquid substance circulation (mixing) device 1 according to the invention affords excellent circulation, this particular type of container 28 in this particular application substantially reduces the dialysis time.

In another field, the reservoir 32 is provided for containing carriers and microcarriers. For example, in the field of cell culture, the cells on (micro)carriers can be confined in a culture zone 32 which will be fed by the swept medium brought into circulation by the liquid substance circulation (mixing) device 1 according to the invention. A grille, filter or membrane (not shown) can be provided for retaining these within the internal reservoir 32. In this case, the addition tube 31 allows for example the inoculation of carriers or microcarriers with cells. Advantageously, the grille, filter or membrane also prevent the cells from circulating in the space internal to the container 18 and external to the reservoir 32 and prevents the cells from the entering the circulation device.

In this type of application, provision is made for the medium to be able to circulate through the internal reservoir 32 in order to nourish the cells. Since homogenization is maximum and circulation is optimum, the medium is perfectly stirred and the cells are well supplied with nutriments. The tube 30 can also serve to enrich the medium with nutriment, and to add regulation substances, As mentioned before, it may be advantageous to provide for the presence of sensors in order to monitor the culture parameters such as the nutriment concentration, the pH, the dissolved oxygen, etc. In addition, provision can also be made to add a fluid inlet in the bottom portion which allows an entry of a liquid or a gas into the compartment 18. In the case when oxygen is fed, the oxygen will be stirred with the medium and the dissolution of the oxygen in the culture medium will be increased. In addition, this stirring significantly reduces the size of any bubbles present, which reduces any damage to the cells through the stresses normally generated by the bubbles.

Figure 11:
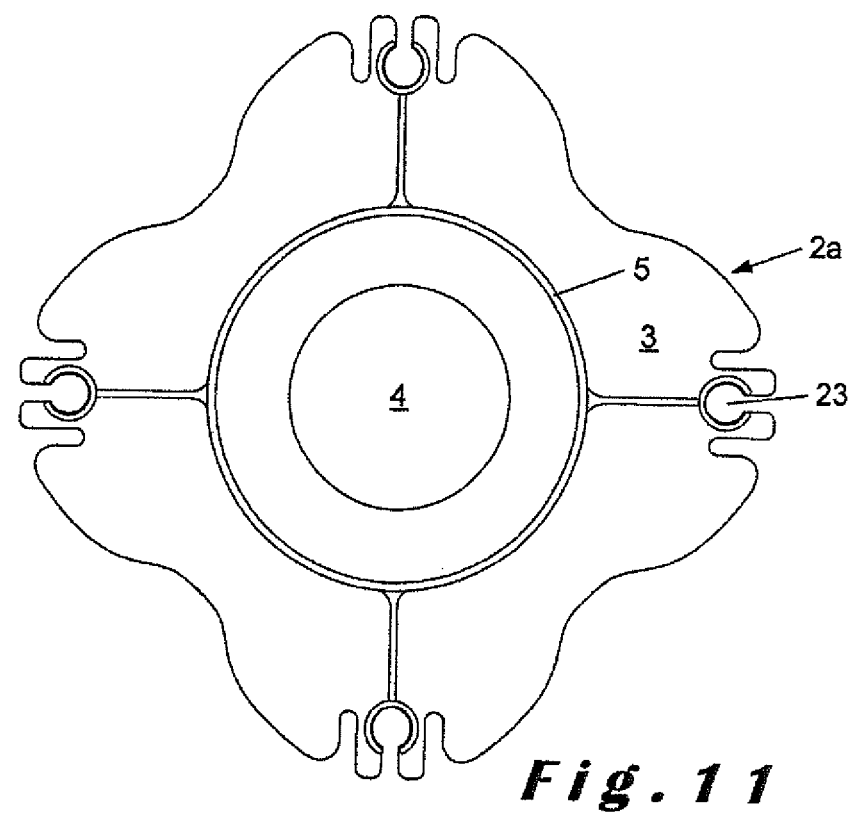
FIG. 11 is a top view of the upper portion of an alternative embodiment of the liquid substance circulation (mixing) device according to the invention.

FIG. 11 illustrates the upper portion 2a of an alternative embodiment of the liquid substance circulation (mixing) device according to the invention wherein the liquid substance inlet 4 is bored through the upper plate 3 under the guiding means 5.

Figure 12:
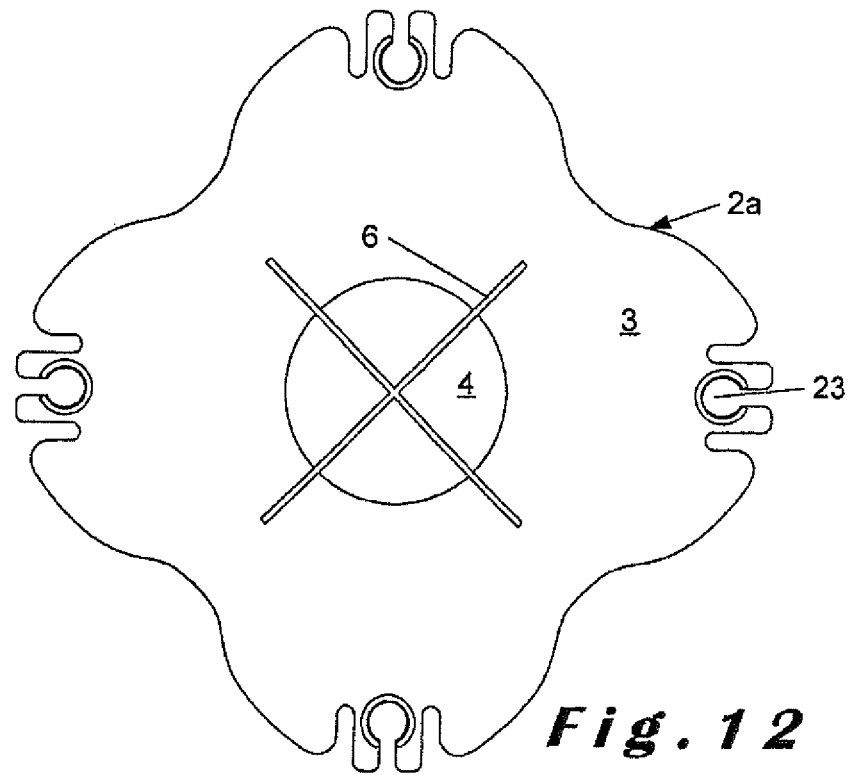
FIG. 12 is a top view of the upper portion of another alternative embodiment of the liquid substance circulation (mixing) device according to the invention.

FIG. 12 illustrates the upper portion 2a of another alternative embodiment of the liquid substance circulation (mixing) device according to the invention comprising the anti-vortex means 6 without guiding means.

FIG. 13 consists of two schematic views (one from above (a) and one axial cut (b) through a plane comprising the axis of the device) of a mixing device adapted for the "free positioning" embodiment of the present invention. In this embodiment, the mixing device (1) is not fitted or otherwise welded to the bag. Rather, the device comprises a positioning mechanism as described earlier in the specification. The advantage of this version of the mixing device is the limited welding to the bag, thus limiting risks of leakages for poor welds.

This positioning mechanism includes extension arms (33) equipped with magnets (34) which are adapted to interact with corresponding magnets (35) located outside of the bag (28), perhaps in the rigid container used to handle the flexible bag (28). When the magnets are engaged, the mixing device (1) is positioned correctly versus the magnetic driver (36) also located outside the bag (28) and perhaps in said rigid container.

The views are namely schematic due to the fact that the magnets (34) should not be visible in FIG. 13a (since they are located under the extension arms (33)) and also because the magnetic impeller is not shown in FIG. 13b—while it should since it is inside the device (1).

Before engagement with the driver, the mixing device may be held in place inside the bag both through the fact that the bag has been pout under vacuum and through the use of a protective cover as described earlier in the specification.

Figure 14:
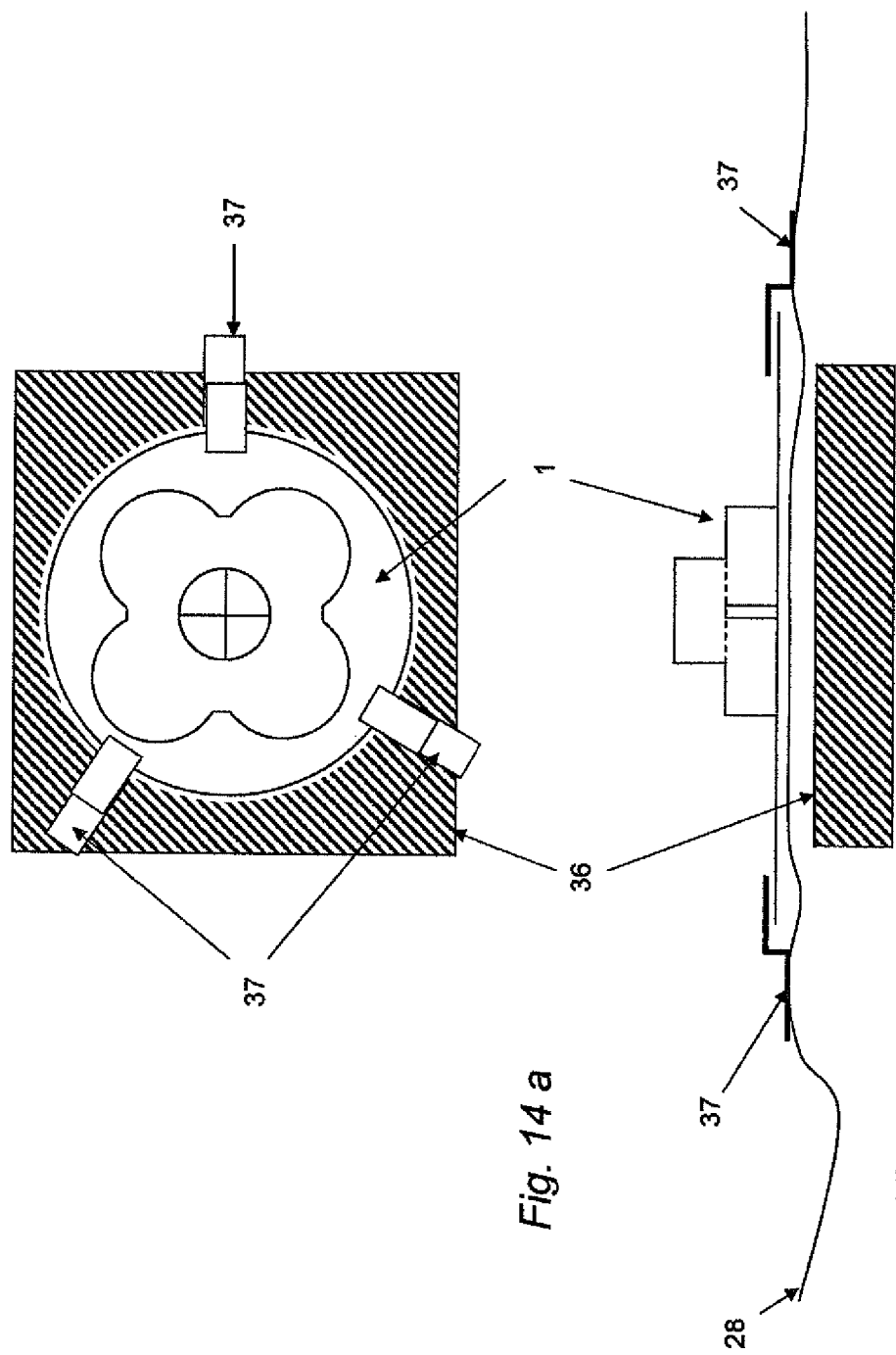

An alternative form of positioning mechanism is illustrated in FIG. 14 which also comprises two schematic views (as defined above) of an embodiment of the invention. This mixing device is also adapted for the "free positioning" embodiment of the present invention. This positioning mechanism comprises three (3) tabs (37) which are fixed (e.g., welded) to the flexible bag (28). The mechanism can include two or more tabs. The geometry of the tabs (37) and the manner in which the mixing device (1) is inserted in them allows the mixing device (1) to move to some extent horizontally relative to the bag side wall (28) before engagement with the driver (36). The limited freedom to move permits the proper positioning of the device for coupling to the driver (36), which coupling occurs through the magnetic forces exerted by the driver on the impeller and vice versa.

FIGS. 15 and 16 (both also comprising 2 schematic views as defined above, but where the axial plane for the cut in figure (b) passes through the magnets) illustrate a rotary magnetic element (8) intended to be retained in a device according to another embodiment of the invention. In this embodiment, already described above, the element (8) is in the form of a disc (alternative to the shape of an impeller) having embedded therein and disposed symmetrically about its axis of rotation, four (4) magnets (11). Again, magnets (11) should not appear on figures "a" because they are embedded in the disc; they are only shown to show their location. Alternatively, one or more such magnets can be used. This disc has portions in relief in the shape of four (4) blades (38). Alternatively, one or more such blades can be used. hi FIG. 15, the blades (38) are curved. In FIG. 16, the blades (38) are straight. This latter embodiment allows rotation of the element in both clockwise and counter-clockwise directions with identical performances.

FIGS. 17a to d relate to two different embodiments of the mixing device where the compartment has no complete bottom surface (bell embodiment).

FIGS. 17a and b (again comprising 2 schematic views as described above) illustrate a mixing device without bottom plate suitable for the "free positioning" version of the present invention. The device simply comprises a top wall (2a) and side wall portions (19) with a convex external surface (21). The side wall portions (19) are merely lying on the bottom of the flexible bag (not shown). Although the device shows four side wall portions, one or more could be utilized.

The portions define slots (20) between them. In the case of one portion, the slot would be located on one position on the portion. In this mixing device, the medium to be agitated is sucked in through inlet openings (4) and is propelled outside the device through the slots (20) all through the centrifugal effect generated by rotary magnetic element (8) rotating within the compartment of the device. In this embodiment, the element rotates about a protrusion (13) extending from the top wall (2a) of the mixer. The element (8) is retained on the protrusion (13) by connection means (22). Alternatively, the element can be a magnetic stir bar or other magnetic agitator that sits on the surface of the flexible bag or other container. The device illustrated is equipped with positioning means including both extension arms (33) and bridges (37)

The alternate embodiment of the device of the present invention illustrated in FIGS. 17c and 17d is quite similar to the device of FIGS. 17a and 17b. However, in this embodiment, a foundation disc (1') is provided below the side wall portions (19) of the mixing device (1). This foundation disc (1') is preferably shaped in a circle and its surface extends from about the inside wall of the side wall portions to the outside wall of the side wall portions. It can have a rim that extends a few centimetres inside or outside of this region to assist in creating a coupling seal to the surface of the bag. The foundation disc can be shaped in a variety of ways such as circular, square or otherwise, but always with a "hole" in the middle thereof below the area of rotation of the element (8). If positioning means are not used with this device, the foundation disc can be used as a surface to weld the mixing device (1) to a container surface. Hence this particular embodiment is adapted for both the "precise positioning" and the "free aligning" versions of this invention.

The "precise location" embodiment is illustrated in FIG. 17e, where the mixing device (1) is shown as being welded to a flexible bag (28) retained in a rigid container (28'). The weld is made between the foundation disc (1') and the bag (28).

FIG. 18 illustrates various alternative embodiments of the side wall portions (19) of a mixing device suitable for the present invention. Each side wall portion (19) includes a section (when viewed in a plane parallel to the bottom of the mixing device) with a shape that includes deflecting means to alter the natural flow path of liquid as it exits slots (20). The shapes include triangles (18a) and half moons (18b) (as described above) but can include many other shapes that provide for the deflection means. Various other side wall portion designs are illustrated in FIGS. 18d to 18i. These geometries all have in common the fact that they include deflecting means either by the shape/thickness of the wall portions itself (FIG. 18a to 18d) and/or by the fact that they have an excrescence (like a baffle) integrally moulded with said wall portions (FIG. 18e to 18i). FIG. 18c shows an embodiment where the deflection means are formed from the wall of the slots (20) which are formed as channels in an annular side wall. In this embodiment, liquid is forced to deflect away from the normal rotational flow path due to the channel-like slots (20).

Figure 18A:
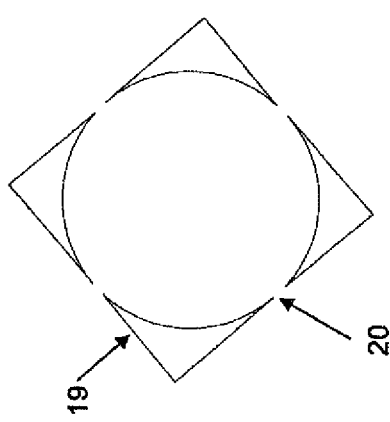
Figure 18B:
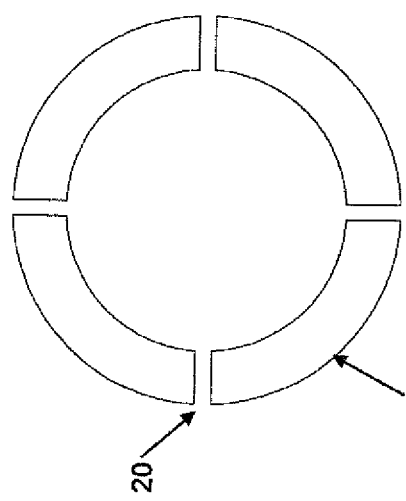
Figure 18C:
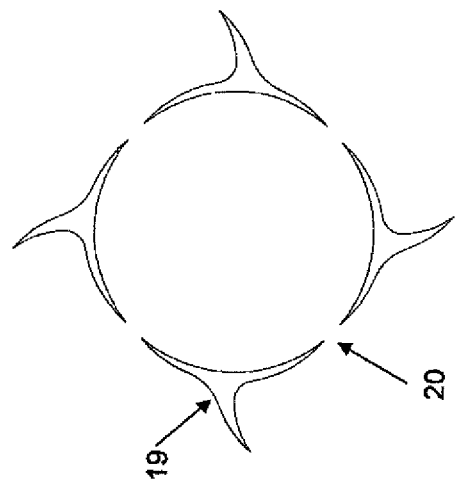
Figure 18D:
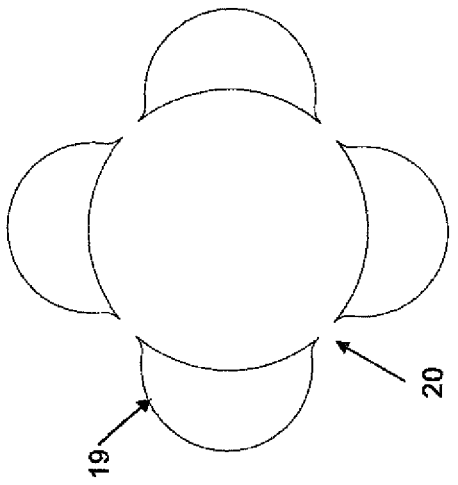
Figure 18E:
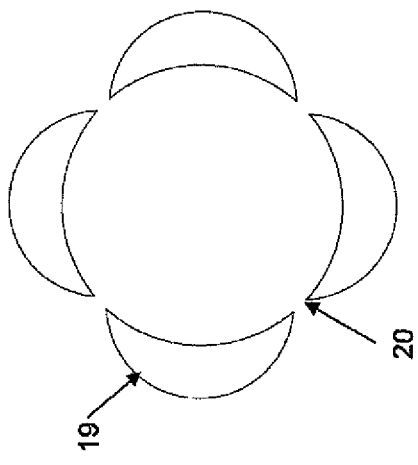
Figure 18F:
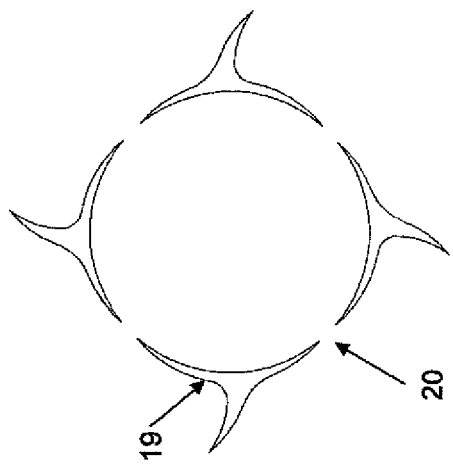
Figure 18I:
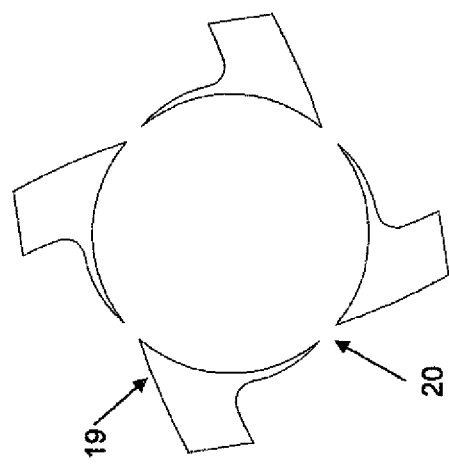
Figure 18H:
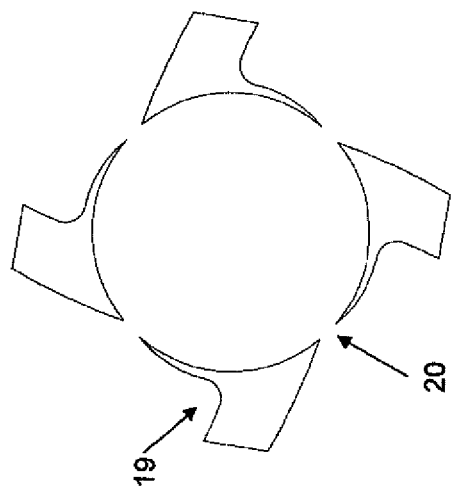
Figure 18G:
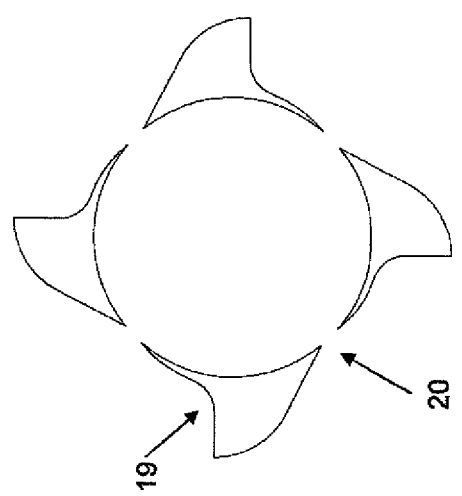
Figure 18K:
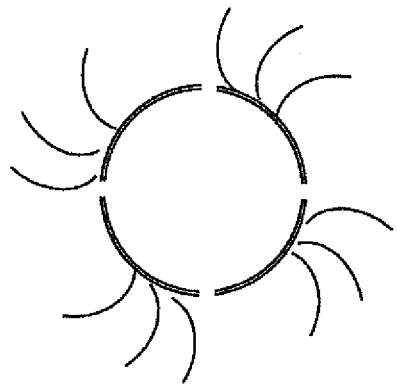
Figure 18M:
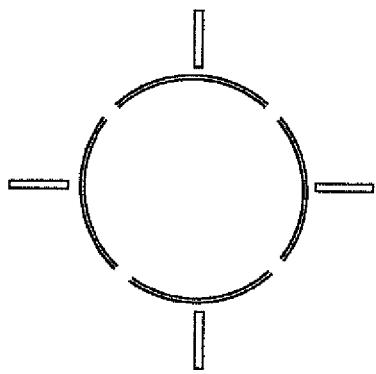
Figure 18J:
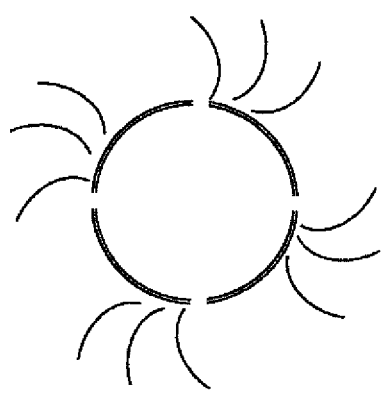
Figure 18L:
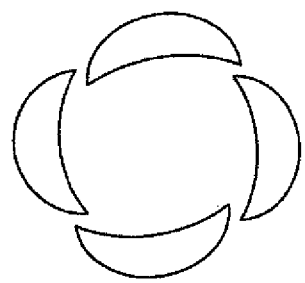

FIGS. 18j to 18m show still further embodiments of deflecting means, namely:
- FIGS. 18j and 18k: external baffles (i.e. not integrated to the wall portions of the mixing device but to the flexible bag, which is not shown) located in the outlet flow and which are curved
- FIG. 18l: half moons but which are offset so that the inner section of the mixing device is no longer circular
- FIG. 18m: external baffles located in the outlet flow but which are straight and distributed evenly approximately at the middle of each side wall portion While the former drawings are related to embodiments of mixing devices with radial outflow directions (where the liquid flows out of the device through its side walls), the embodiments of FIG. 19 (which consists in schematic axial cuts) show axial outlet directions (the liquid flowing out through peripheral points on top surface of the device). FIG. 19a shows an embodiment of the mixing device with an axial central inlet and axial peripheral outlets (see arrows) and having an internal baffle (39). FIG. 19b shows the same embodiment without an internal baffle. FIG. 19c shows the same embodiment as FIG. 19a but with guiding means (5) upstream of the inlet to increase the vertical action of the device. FIG. 19d shows the same embodiment but with guiding tubes (40) at the outlets, said tubes prolonging said outlets and transforming the axial outflow directions in radial outflow directions.

FIG. 20 shows a trolley that can be used in a "precise location" embodiment in cooperation with an intermediate frame as the one pictured in FIGS. 21 to 23 and comprising:
a body (40) supporting a driver (36);
at one end of the body, 2 wheels (41) intended to roll on the floor;
at least one foldable foot (42) bearing a wheel (43) which rolls on the floor when the trolley is disengaged from a container (like the one shown in FIGS. 22 and 23) and which folds back when the trolley is engaged with the container; and
at the other end of the body, 2 wheels (44) which are never in contact with the floor but are able to roll on the rail of a frame (45) like the one of FIG. 21 when the trolley is engaged with the container.

At the end close to wheels (41) rolling on the floor, the trolley comprises a handle (46) in order to be able to move it easily. At the same end, it also comprises a support (57) for the controller of the driver and hanging means for hanging said end of the trolley to the container in order to put and keep the driver at its right location against the bottom of the container. These hanging means comprise hooks (47) collaborating with springs (48).

The intermediate frame (45) shown in FIGS. 21 to 23 comprises a guiding rail comprising a bottom plate (49) and 2 side plates (49'). In FIG. 21, the rail is shown straight (because this figure is schematic) but in fact, it is inclined as shown in FIGS. 22 and 23. This guiding rail is equipped with 2 locking castors (50) collaborating with matching holes on the trolley (not shown). The intermediate frame (45) of FIG. 7 also comprises a compartment (51) for tubing security which can be closed by folding back movable plate (52) and 4 hollow upward extensions (53) designed to receive the feet (54) of the rigid container (55) pictured in FIGS. 22 and 23.

Compartment (51) and movable plate (52) are not present in the frame shown in FIGS. 22 and 23. These figures show the trolley of FIG. 20 and another intermediate frame (45)

mounted on the rigid container (55) respectively in a schematic view and in a view from above, with the container in phantom (i.e. shown as a transparent item, which is generally not the case). As can be seen, frame (45) is inserted between said container (55)—which rests with its feet (54) in the hollow extensions (53)—and a roller plate (56) which is a standard one, into which the container (55) directly fits as well.

In these figures, the trolley is shown in a position such that the driver (36) is at a precise location relative to the container, which is underneath its bottom and substantially in the centre of it. It is kept there thanks to the locking castors (50) and the hanging means consisting of the hooks (47) and springs (48). As can be seen on these figures, the foldable foot (42) has come down after it has passed the beam (55') of the container but since the trolley is hanged up, it does not touch the floor. The same applies to wheels (41).

FIG. 24 shows schematic views of a rigid container, with (24a and b) or without (24c and d) wheels (56) and respectively with a square or rectangular bottom frame (24a and c) or with a frame in "U" shape (24b and d) allowing insertion of the driver (36) by the open end of the "U", and hence avoiding to pass underneath the beam (55') formed by the frame.

Although the preferred embodiments of the invention have been disclosed for illustrative purpose, those skilled in the art will appreciate that various modifications, additions or substitutions are possible, without departing from the scope and spirit of the invention as disclosed in the accompanying claims.

The invention claimed is:

1. An apparatus for processing a fluid, comprising:
a flexible bag having an interior for receiving the fluid;
a mixer associated with the interior of the flexible bag;
a first cover attached to the bag and located adjacent to a bottom wall of the bag, the cover including an upper wall and a side wall connected to the upper wall, said upper wall and side wall together forming a compartment receiving the mixer, at least one of said upper wall or said side wall adapted for allowing fluid to pass into the interior of the vessel; and
a second cover for covering the first cover when the bag is folded and for exposing the first cover when the bag is unfolded.

2. The apparatus of claim 1, wherein the first cover is attached to a first wall of the bag, and the second cover is attached to a second wall of the bag generally opposite the first wall.

3. The apparatus of claim 1, wherein the first cover includes an opening in the upper wall.

4. The apparatus of claim 1, wherein the first cover includes an opening in the sidewall.

5. The apparatus of claim 4, wherein the first cover includes a plurality of circumferentially spaced openings in the sidewall forming fluid outlets.

6. The apparatus of claim 5, wherein the openings comprise vertically extending slot.

7. The apparatus of claim 6, further including a generally circular opening in the upper wall forming a fluid inlet, the circular opening including a cross-shapud structure for inhibiting the rormation of a fluid vortex in the opening.

8. The apparatus of claim 1, wherein the mixer comprises at least one blade.

9. An apparatus for processing a fluid, comprising:
a flexible bag including an interior for receiving the fluid;
a rotary mixer for mixing the fluid;
a circulation device in the interior of the flexible bag including a wall forming a compartment for receiving the mixer and including at least one opening for allowing the fluid to contact the mixer in the compartment; and
a cover including a cavity for at least partially receiving the circulation device when the flexible bag is folded.

10. The apparatus of claim 9, wherein the circulation device includes at least one inlet and at least one outlet for circulating the fluid within the compartment including the mixer.

11. The apparatus of claim 10, wherein the at least one inlet is formed in an upper wall of the circulation device and the at least one outlet is formed in a sidewall of the circulation device.

12. The apparatus of claim 10, further including an anti-vortex device associated with the inlet adapted to inhibit vortex formation.

13. The apparatus of claim 9, wherein the cover includes a cavity that matches the shape of the circulation device.

14. The apparatus of claim 9, wherein the bag includes a first wall and a second wall, wherein the cover is attached to the first wall and the circulation device is attached to the second wall.

15. An apparatus for processing a fluid, comprising:
a flexible bag having an interior for receiving the fluid, the flexible bag including a bottom wall;
a rotary mixer associated with the interior of the flexible bag;
a first cover attached to the bag, the cover including an upper wall and a sidewall together forming a compartment for receiving the mixer; and
a protrusion within the compartment of the first cover for supporting the mixer above the bottom wall of the bag.

16. The apparatus of claim 15, wherein the bottom wall of the flexible bag is connected to the sidewall of the cover.

17. The apparatus of claim 15, further including a bearing connected to the protrusion.

18. The apparatus of claim 15, wherein the rotary mixer comprises at least one blade.

19. The apparatus of claim 15, wherein the rotary mixer comprises a magnetic impeller.

20. The apparatus of claim 15, wherein at least one of the upper wall and the sidewall includes an opening.

21. An apparatus for processing a fluid, comprising:
a flexible bag including an interior for receiving the fluid;
a rotary mixer for mixing the fluid;
a circulation device including a wall forming a compartment for receiving the mixer and including at least one opening for allowing the fluid to contact the mixer in the compartment; and
a cover including a cavity for at least partially receiving the circulation device when the flexible bag is folded,
wherein the bag includes a first wall and a second wall, wherein the cover is attached to the first wall and the circulation device is attached to the second wall.

22. The apparatus of claim 1, wherein the first cover is attached to the bottom wall.

* * * * *

UNITED STATES PATENT AND TRADEMARK OFFICE
CERTIFICATE OF CORRECTION

PATENT NO.        : 8,845,181 B2                                        Page 1 of 1
APPLICATION NO.   : 13/615727
DATED             : September 30, 2014
INVENTOR(S)       : Castillo et al.

It is certified that error appears in the above-identified patent and that said Letters Patent is hereby corrected as shown below:

In the Claims

Column 35, line 56, please replace "slot" with -- slots --.

Column 35, line 59, please replace "shapud" with -- shaped --.

Column 35, line 60, please replace "rormation" with -- formation --.

Signed and Sealed this
Second Day of June, 2015

Michelle K. Lee
*Director of the United States Patent and Trademark Office*